US011540987B2

(12) United States Patent
Brouard et al.

(10) Patent No.: US 11,540,987 B2
(45) Date of Patent: Jan. 3, 2023

(54) COMPOSITION WITH STABILIZED TASTE AND ODOR (II)

(71) Applicant: SYMRISE AG, Holzminden (DE)

(72) Inventors: Denis Brouard, Saint Ouen (FR); Sandra Gaebler, Höxter (DE); Martina Herrmann, Hameln (DE)

(73) Assignee: Symrise AG, Holzminden (DE)

( * ) Notice: Subject to any disclaimer, the term of this patent is extended or adjusted under 35 U.S.C. 154(b) by 330 days.

(21) Appl. No.: 15/781,321

(22) PCT Filed: Dec. 16, 2015

(86) PCT No.: PCT/EP2015/079990
§ 371 (c)(1),
(2) Date: Jun. 4, 2018

(87) PCT Pub. No.: WO2017/101994
PCT Pub. Date: Jun. 22, 2017

(65) Prior Publication Data
US 2020/0179252 A1    Jun. 11, 2020

(51) Int. Cl.
A61K 8/35      (2006.01)
A23L 33/12     (2016.01)
A23D 9/007     (2006.01)
A23L 3/3499    (2006.01)
A61K 8/36      (2006.01)
A61Q 1/00      (2006.01)
A61Q 1/06      (2006.01)
A61Q 1/10      (2006.01)
A61Q 5/02      (2006.01)
A61Q 5/12      (2006.01)
A61Q 19/00     (2006.01)
A61Q 19/02     (2006.01)
A61Q 19/08     (2006.01)
A61Q 19/10     (2006.01)
C11B 5/00      (2006.01)

(52) U.S. Cl.
CPC ........... *A61K 8/35* (2013.01); *A23D 9/007* (2013.01); *A23L 3/3499* (2013.01); *A23L 33/12* (2016.08); *A61K 8/361* (2013.01); *A61Q 1/00* (2013.01); *A61Q 1/06* (2013.01); *A61Q 1/10* (2013.01); *A61Q 5/02* (2013.01); *A61Q 5/12* (2013.01); *A61Q 19/007* (2013.01); *A61Q 19/02* (2013.01); *A61Q 19/08* (2013.01); *A61Q 19/10* (2013.01); *C11B 5/0035* (2013.01); *A23V 2002/00* (2013.01)

(58) Field of Classification Search
None
See application file for complete search history.

(56) References Cited

U.S. PATENT DOCUMENTS

2014/0178536 A1*  6/2014  McNeill .............. A23G 9/322
                                                    426/103

FOREIGN PATENT DOCUMENTS

WO   WO 2014/135650   *  9/2014  ............ A01N 35/04
WO      2015/144332 A1    10/2015
WO      2015/144333 A1    10/2015

OTHER PUBLICATIONS

Waddell et al. (Food Technology 61:22-61, 2007) (Year: 2007).*
Prandini etal (J Food Composition and Analysis 24:55-61, 2011) (Year: 2011).*
Quinn et al., "Antioxidant Properties of Phenolic Compounds in Macadamia Nuts," JAOCS vol. 73, No. 11, Nov. 30, 1996, pp. 1585-1588.
Moodley et al., "Elemental composition and chemical characteristics of five edible nuts (almond, Brazil, pecan, macadamia and walnut) consumed in Southern Africa," Journal of Environmental Science and Health, Part B: Pesticides 42(5), Jun. 11, 2007 pp. 585-591.
Loughran, "Natural Ingredients for Skin Care," Natural Skin Care: Alternative and Traditional Techniques, Jan. 1, 2002, pp. 101-110.
Christie, "Separation of Molecular Species of Triacylglycerols by High-Performance Liquid Chromatography with a Silver Ion Column," Journal of Chromatography, vol. 454, Jan. 1, 1988, pp. 273-284.

* cited by examiner

*Primary Examiner* — Craig D Ricci
(74) *Attorney, Agent, or Firm* — Dilworth & Barrese, LLP

(57) ABSTRACT

Suggested is a composition with stabilized taste and/or odor, comprising (a) at least one acetophenone derivative of formula (I) wherein $R_1$ stands for hydrogen or methyl, and $R_2$ stands for hydrogen, hydroxyl or a —$OCH_3$ group, or a cosmetically pharmaceutically acceptable salt thereof, and (b) at least one mono- or polyunsaturated $C_8$-$C_{22}$ fatty acid or its monohydric polyhydric $C_1$-$C_{18}$ alkyl alcohols ester.

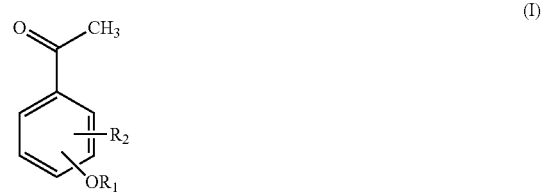

8 Claims, No Drawings

COMPOSITION WITH STABILIZED TASTE AND ODOR (II)

FIELD OF INVENTION

The present invention belongs to the field of cosmetic products and food products and refers to compositions comprising selected acetophenone derivative for stabilizing the taste and/or odor of the contained fatty acids and esters thereof, as well as the personal care products and food products comprising the said compositions with stabilized taste and/or odor.

STATE OF THE ART

Fatty acids (esters) are the main constituents of oils and fats. They possess a simple structure consisting of a long hydrocarbonate chain with about 12-22 carbon atoms and one or more carboxylic (acyl) groups. According to the number of the present double bonds between the carbon atoms fatty acids (esters) are generally divided into saturated, monounsaturated and polyunsaturated fatty acids (esters). At present most fatty acids (esters) are obtained from natural origin including vegetable and animal origin, such as hard animal fats, coconut oil, palm kernel oil and soybean oil. The most common naturally occurring fatty acids are palmitic, stearic, oleic and linoleic acids. With the exception of the tropical oils such as palm and coconut oil, the majority of fatty acids (esters) in most plant- and animal-derived oils of commercial significance contain eighteen carbon atoms. Other fatty acids (esters) belong to synthetic compounds obtained from petroleum. Thanks to the beneficial physical and biological properties, the application of fatty acids (esters) is overwhelming.

Fatty acids (esters) are of great importance in cosmetics industry and becoming more and more commonly used components in many cosmetic formulations for daily care of the face, body and hair. Naturally occurring fatty acids (esters) are components of skin and are components of a complex mixture that makes up the outermost layer. Because of their oiling, softening, smoothing and protective properties, fatty acids (esters) can prevent water loss through the skin, mainly by means of making a protective layer on the epidermis. Additionally they soften the stratum corneum and reduce inflammation of the skin, thereby weakening the sensation of pain. However with increasing age the natural synthesis of cutaneous fatty acids (esters) declines, which causes that skin excessively dehydrates. In order to avoid the unwanted drying of skin caused by the deficiency in fatty acids (esters), in most marketed cosmetic products fatty acids (esters) are applied as an indispensable cosmetic components.

Besides the application in the field of cosmetics, fatty acids (esters) also play a key role in food and nutrition industry, because of their biological effects in proper functioning of the human body—in metabolism as major metabolic fuel (storage and transport of energy), as essential components of all membranes, and as gene regulators. The edible fatty acids (esters) mostly belong to polyunsaturated fatty acids, which are not metabolically synthesized in mammals and therefore termed as "essential fatty acids". It has been reported that for human the minimum intake to avoid clinical symptoms of deficiency, taking "ω-3" fatty acids (such as docosahexaenoic acid (DHA) and eicosapentaenoic acid (EPA)) as an example, is approximately 0.5 g per day. In addition it has been proved by many epidemiological and experimental studies that the additional intake of "essential fatty acids" has significant beneficial effects. In order to satisfy the huge requirement of consumers on the essential fatty acids (esters) there are increasing number of various food and nutritional products in the market, which supply enough amount of the essential fatty acids (esters).

Although the application of fatty acids (esters) in cosmetic products and food products is mature technology, there are still some unsolved problems mainly concerning the complex storage of raw materials and the limited shelf-life of the end product, which is caused by the rancidity of the contained unsaturated fatty acids (esters). Rancidification is the process which causes a substance to become rancid, meaning having a rank, unpleasant smell or taste. Specifically, it is considered to be the hydrolysis and/or oxidation of fats into short-chain aldehydes and ketones, which are mostly volatile and objectionable in taste and odour. This process results in the rancidity of the fatty acids (esters) and the end products. It is obvious that oils and fats containing rancid fatty acids (esters) cannot be further processed into corresponding end products, and the rancid end products cannot be sold on market or used by the consumer any more. Both of them lead to the increase of production costs, which is unacceptable both by the manufacturer and the consumers.

In order to avoid or weaken the rancidity of fatty acids (esters) many methods have been carried out. For example in industry antioxidants are often used as preservatives in fat-containing foods or cosmetics to delay the onset or slow the development of rancidity due to oxidation. From the state of the art numerous publications are also known to solve the rancidity-problem.

The patent application KR 20100105234 reported a composition for preventing rancidity of unsaturated fatty acids, which comprises potassium chloride, potassium carbonate, magnesium chloride, calcium lactate and sodium citrate.

The international patent application WO 92/22282 disclosed oil components for cosmetic and/or pharmaceutical preparations. This published oil components consist entirely or mainly of Guerbet carbonates. Such oil components not only have good compatibility with the skin and mucous membrane but are also highly stable with respect to rancidity.

In the patent application US 2005/0244564 a method is described to increase the oxidative stability of oil-containing food products. Based on the discovery that higher level of oleic acid and lower level of linoleic acid contribute to improving the oxidative stability, the disclosed method is characterized by the addition of an oil rich in ω-3 fatty acid to a product with large ratio between oleic acid and linoleic acid.

The subject matter of patent application GB 813, 538 A refers to the use of 5-acenaphthenol as an antioxidant for eliminating the deleterious effects of oxidation and improving the stability of oxidizable compositions including solid fats, fatty oils and so on.

U.S. Pat. No. 2,521,856 A provided a new mixture comprising (a) butylated hydroquinone monoalkyl ether wherein the alkyl group contains from 1 to 4 carbon atoms inclusive; (b) hydroquinione and (c) an acidic material selected from the group consisting of citric acid, ascorbic acid, oxalic acid, phosphoric acid, ethyl acid phosphate and triethyl phosphate to improve the stabilization of materials normally subject to oxidative rancidity due to their content of glycerides of fatty acids.

In the patent application GB 595838 A stabilised edible vegetable, animal, fish oil, fats and waxes are provided, wherein the mentioned edible materials were brought into contact with a small portion of thio-di-saturated fatty acid, or ester, amide, salt, or anhydride thereof.

GB 618409 A disclosed nordihydroguaiaretic acid of vegetable origin as antioxidant to preserve lard, butter, edible oils and the like in a fresh and edible condition for long periods so as to permit packaging in sealed containers and storage in hot climatic conditions for long periods.

Although, there are already several fatty acids (esters) containing compositions reported with good stability with respect to rancidity, most of them are based on increasing the ratio of saturated fatty acids in the obtained composition. However the rate of saturated to unsaturated fatty acids is very important for human nutrition. That means high levels of saturated fatty acids are on the one hand desirable to increase stability of fatty acids (esters), while on the other hand undesirable e.g. nutritionally, because high levels of saturated fatty acids are frequently considered do have influence by increasing the concentration of low density lipoproteins (LDL), affecting the ratio of LDL to HDL (high density lipoproteins), promoting clotting and vascular smooth muscle proliferation.

Therefore there is a significant need to find a novel fatty acids (esters)-containing composition with stabilized taste and/or odor as well as improved resistance to oxidation and rancidity. With the utilization of the fatty acids (esters)-containing composition, a more effective storage of fatty acids (esters) as raw materials and longer shelf-life of the end product comprising fatty acids (esters) would be realized, without intentionally decreasing the level of unsaturated fatty acids (esters). The new composition shall maintain all the excellent physical and biological properties of the contained fatty acids (esters) and further possess excellent resistance to rancidity. Preferably the used stabilizing agent contained in the composition should be of defined chemical structure and purity, toxicologically safe in use, well tolerated, effective already at low concentrations, easy to formulate, colorless and odorless.

Based on the known important benefit of fatty acids (esters)-containing composition with stabilized taste and/or odor in the cosmetic and food industry, the main problem underlying the present invention has been providing a new composition comprising fatty acids (esters), wherein the unsaturated fatty acids (esters) contained still express their original physical and biological properties and are well protected from oxidation and rancidity. Another problem solved by the present invention has been providing a new method to preserve unsaturated fatty acids (esters) from oxidation and rancidity. Besides a further problem underlying the present invention has been supplying cosmetic and food products with better resistance to rancidity and longer shelf-life.

DESCRIPTION OF THE INVENTION

Object of the present invention is a composition with stabilized taste and/or odor comprising (a) at least one acetophenone derivative of formula (I)

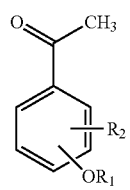

(I)

wherein
$R_1$ stands for hydrogen or methyl, and
$R_2$ stands for hydrogen, hydroxyl or a —$OCH_3$ group, or a cosmetically or pharmaceutically acceptable salt thereof, and (b) at least one mono- or polyunsaturated $C_8$-$C_{22}$ fatty acid or its monohydric or polyhydric $C_1$-$C_{18}$ aliphatic alcohols ester The amount of acetophenone derivative of formula (I) in the compositions according to the present invention is in the range from about 0.01 to 5 wt. %, preferably in the range from 0.05 to 2 wt. %, and particularly preferably in the range from 0.1 to 1 wt. % relative to the total weight of the composition.

It has been surprisingly observed that, though acetophenone derivatives of formula (I) as a known antioxidant has much weaker antioxidant activity to the conventional antioxidants such as alpha-tocopherol, even at a low concentration acetophenone derivatives of formula (I) shows a superior activity to preserve various mono- or polyunsaturated $C_8$-$C_{22}$ fatty acids and esters thereof from rancidity than other antioxidants.

Acetophenone Derivatives

Acetophenone derivatives according to the present invention represent known compounds that can be obtained by ordinary methods of organic chemistry. It is understood that both substituents $OR_1$ and $R_2$ can be located in ortho, meta or para position towards the methylketo group.

Preferably, the species are selected from the group consisting of

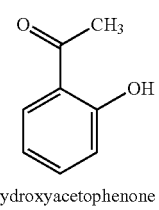

(Ia)

2-hydroxyacetophenone

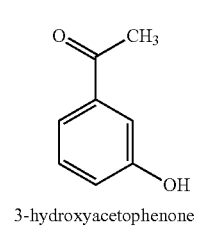

(Ib)

3-hydroxyacetophenone

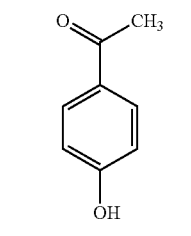

(Ic)

4-hydroxyacetophenone or their mixtures. In as far the definition refers to cosmetically or pharmaceutically acceptable salts of said derivatives, this means that these salts can be safely used for pharmaceutical purposes. This does not mean that the present invention or any aspect thereof is restricted to the use of a compound of formula (I) or a corresponding mixture for pharmaceutical purposes. Generally, if a salt can be used for pharmaceutical purposes it can likewise be used for cosmetic purposes, or in food or beverage formulations. In particular, the sodium and potassium and ammonium salts of compounds of formula (I) are considered as (pharmaceutically) acceptable salts. In some cases the utilization of the respective ionic compound or solvate carrier proves to be superior to the unmodified derivative. The (pharmaceutically) acceptable salts (and the corresponding solvates) of compounds of formula (I) can be prepared by standard procedures. Hereinafter, any reference to a compound of formula (I) or a corresponding mixture as defined above is to be understood as comprising an additional reference to corresponding (pharmaceutically) acceptable salts thereof.

In a preferred embodiment the composition comprise or contain two or three of the compounds (Ia), (Ib) and (Ic), as for example 2-hydroxyacetophenone and 3-hydroxyacetophenone, or 2-hydroxyacetophenone and 4-hydroxyacetophenone, or 3-hydroxyacetophenone and 4-hydroxyacetophenone In a most preferred embodiment the composition of the present invention comprise 4-hydroxyacetophenone.

Unsaturated Fatty Aid and Ester Thereof

Unsaturated fatty acid and ester thereof as component (b) according to the present invention refer to mono- or polyunsaturated $C_8$-$C_{22}$ fatty acid and its monohydric or polyhydric $C_1$-$C_{18}$ aliphatic alcohols ester.

Preferably the component (b) of the composition according to the present invention comprises:

(b-1) at least one acyl compound of formula (II)

(II)

wherein
R stands for hydrogen atom or a $C_1$-$C_{18}$ alkyl group and X represents a mono- or polyunsaturated $C_8$-$C_{22}$ acyl group,
and/or
(b-2) at least one acylglycerol compound of formula (III)

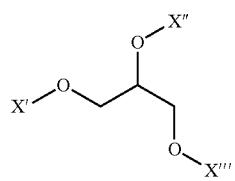
(III)

wherein
X', X" and X''' independently of one another represents a hydrogen atom or a saturated or mono- or polyunsaturated $C_8$-$C_{22}$ acyl group,
with the proviso that X', X" and X''' do not simultaneously represent hydrogen atom and at least one of X', X" and X''' being unsaturated acyl group.

Acyl Compound

According to the present invention the acyl compound of formula (II) as component (b-1) includes mono- or polyunsaturated $C_8$-$C_{22}$ fatty acids and their esters of $C_1$-$C_{18}$ alcohols.

The typical representatives of component (b-1) comprise but not limited to palmitioleic acid (C16: 1), oleic acid (C18: 1), elaidic acid (C18: 1), ricinoleic acid (C18: 1), petroselinic acid (C18: 1), vaccenic acid (C18: 1), linoleic acid (C18: 2), α-linolenic acid (C18: 3), γ-linolenic acid (C18: 3), cis-linolenic acid (C18: 3), punicic acid (C18: 3), oleostearynic acid (C18: 3), stearidonic acid (C18:4), gondoci acid (C20: 1), gadoleic acid (C20: 1), paullinic acid (C20: 1), arachidonic acid (C20: 4), erucic acid (C22: 1), EPA (C20: 5), docosapentaenoic acid (C20: 5), DHA (C22: 6), myristyl oleate, myristyl erucate, cetyl oleate, cetyl erucate, stearyl oleate, stearyl erucate, isostearyl oleate, oleyl myristate, oleyl palmitate, oleyl stearate, oleyl isostearate, oleyl oleate, oleyl behenate, oleyl erucate, behenyl oleate, behenyl erucate, erucyl myristate, erucyl palmitate, erucyl stearate, erucyl isostearate, erucyl oleate, erucyl behenate and erucyl erucate.

In a preferred embodiment of the present invention in acyl compound of formula (II) R is hydrogen atom and X is a mono- or polyunsaturated $C_{16}$-$C_{22}$ acyl group.

In a most preferred embodiment of the present invention the component (b-1) is oleic acid, linoleic acid, γ-linolenic acid, α-linolenic acid, EPA and DHA.

Linoleic acid occurs most abundantly in sunflower oil, soybean oil, safflower, corn oil, sesame oil, peanut oil, grape seed oil and wheat germ oil. It is essential to the skin's barrier function. In dry skin it strengthens the lipid barrier of epidermis, protects against transepidermal loss of water and normalizes the skin metabolism. In persons with acne skin, a decrease in linoleic acid content in sebum is observed, which leads to blocked pores and formation of comedos and eczemas. The use of linoleic acid for oily skin and problematic skin care leads to improvement of the work of sebaceous glands, unblocking of pores and decrease in the number of comedos.

[-linolenic acid belongs to omega-6 series and can be obtained from natural sources including borage oil, black currant oil, evening primrose oil and hemp oil. Besides α-linolenic acid is a representative of omega-3 group and is found in linseed oil, soybean oil, rapeseed oil, wheat germ oil, walnut oil, and algae and marine phytoplankton. Both α- and γ-linolenic acids are physiological components of cell membranes or mitochondria membranes in human cells.

Polyunsaturated fatty acids such as eicosapentaenoic acid (EPA) or docosahexaenoic acid (DHA) are found in fish oil from salmon, cod, herring, mackerel and are metabolites of algae and marine phytoplankton.

Acylglycerol Compound

Acylglycerol compounds of formula (III) as component (b-2) of the composition according to the present invention concern mono-, di-, or triglycerides formed from glycerol and $C_8$-$C_{22}$ fatty acids, wherein the fatty acids comprise but not limited to caprylic acid (C8: 0), decanoic acid (C10: 0), lauric acid (C12: 0), myristate acid (C14: 0), palmitic acid (C16: 0), palmitioleic acid (C16: 1), margaric acid (C17: 0), stearic acid (C18: 0), oleic acid (C18: 1), elaidic acid (C18: 1), ricinoleic acid (C18: 1), petroselinic acid (C18: 1), vaccenic acid (C18: 1), linoleic acid (C18: 2), α-linolenic acid (C18: 3), γ-linolenic acid (C18: 3), cis-linolenic acid (C18: 3), punicic acid (C18: 3), oleostearynic acid (C18: 3), stearidonic acid (C18:4), arachidic acid (C20: 0), gondoci acid (C20: 1), gadoleic acid (C20: 1), paullinic acid (C20: 1), arachidonic acid (C20: 4), erucic acid (C22: 1), EPA (C20: 5), docosapentaenoic acid (C20: 5), docosanoic acid (C22: 0), DHA (C22: 6).

The typical representatives of component (b-2) comprise but not limited to tri-, di- or monoglyceryl esters of palmitoleic acid, oleic acid, linoleic acid, linolenic acid, stearidonic acid, eicosapentaenoic acid, docosahexaenoic acid such as e.g. triolein, trilinolein, trilinolenin, 1,3-diolein, 1,2-diolein, 1,3-dilinolein, 1,2-dilinolein, 1,3-dilinolenin, 1,2-dilinolenin, 1-monoolein, 2-monoolein, 1-monolinolein, 2-monolinolein, 1-monolinolenin, 2-monolinolenin and mixed di- or triglyceryl esters such as e.g. glyceryl-1-stearate-3-oleate, glyceryl-1-stearate-2-oleate, glyceryl-2-stearate-1-oleate, glyceryl-1-stearate-3-linoleate, glyceryl-1-stearate-2-linoleate, glyceryl-2-stearate-1-linoleate, glyceryl-1-stearate-3-linolenate, glyceryl-1-stearate-2-linolenate, glyceryl-2-stearate-1-linolenate, glyceryl-1-palmitate-3-oleate, glyceryl-1-palmitate-2-oleate, glyceryl-2-palmitate-1-oleate, glyceryl-1-palmitate-3-linoleate, glyceryl-1-palmitate-2-linoleate, glyceryl-2-palmitate-1-linoleate, glyceryl-1-palmitate-3-linolenate, glyceryl-1-palmitate-2-linolenate, glyceryl-2-palmitate-1-linolenate, glyceryl-1,2-distearate-3-oleate, glyceryl-1,3-distearate-2-oleate, glyceryl-2,3-distearate-1-oleate, glyceryl-1,2-distearate-3-linoleate, glyceryl-1,3-distearate-2-linoleate, glyceryl-2,3-distearate-1-linoleate, glyceryl-1,2-distearate-3-linolenate, glyceryl-1,3-distearate-2-linolenate, glyceryl-2,3-distearate-1-linolenate, glyceryl-1,2-dipalnnitate-3-oleate, glyceryl-1,3-dipalmitate-2-oleate, glyceryl-2,3-dipalmitate-1-oleate, glyceryl-1,2-dipalmitate-3-linoleate, glyceryl-1,3-dipalmitate-2-linoleate, glyceryl-2,3-dipalmitate-1-linoleate, glyceryl-1,2-dipalmitate-3-linolenate, glyceryl-1,3-dipalmitate-2-linolenate, glyceryl-2,3-dipalmitate-1-linolenate, glyceryl-1,2-dioleate-3-stearate, glyceryl-1,3-dioleate-2-stearate, glyceryl-1,2-dilinoleate-3-stearate, glyceryl-1,3-dilinoleate-2-stearate, glyceryl-1,2-dilinolenate-3-stearate, glyceryl-1,3-dilinolenate-2-stearate, glyceryl-1,2-dioleate-3-palmitate, glyceryl-1,3-dioleate-2-palmitate, glyceryl-1,2-dilinoleate-3-palmitate, glyceryl-1,3-dilinoleate-2-palmitate, glyceryl-1,2-dilinolenate-3-palmitate, glyceryl-1,3-dilinolenate-2-palmitate.

In a preferred embodiment of the present invention the acylglycerol compound of formula (III) is a mono-, di-, or triglyceride origined from vegetable oils.

In another preferred embodiment of the present invention the acylglycerol compound of formula (III) is a diglyceride, which mainly origin from vegetable oils, i.e. two of X', X" and X'" of formula (III) independently of one another represents a saturated or mono- or polyunsaturated $C_8$-$C_{22}$ acyl group with the proviso that one of them is unsaturated.

In another preferred embodiment of the present invention the acylglycerol compound of formula (III) is a monoglyceride, which mainly origin from vegetable oils, i.e. one of X', X" and X'" of formula (III) independently of one another represents a mono- or polyunsaturated $C_8$-$C_{22}$ acyl group.

Vegetable oils are liquid vegetable fats that remain in the liquid form at room temperature. These lipids are most commonly extracted from various parts of plants such as seeds, fruits, or plant seedlings. Under the chemical terms they are a combination of triglycerides of higher saturated and unsaturated fatty acids. In other words, these compounds are esters of glycerol and higher fatty acids, containing in their structure long aliphatic carbon chains. According to the present invention the vegetable oils comprise but not limited to Argan oil, Chokeberry (seed) oil, Avocado oil, Peach (pits) oil, Canola oil, Nigella oil, Pumpkin (pumpkin seed) oil, Wild rose (seeds) oil, Pomegranate seeds oil, Jojoba (liquid wax) oil, Cocoa/cocoa butter, Wheat sprout oil, Coconut/coconut butter, Safflower oil, Corn oil, Camelina oil, Flax seed oil, Macadamia oil, Raspberries seeds oil, Meadowfoam seeds oil, Passiflora seeds oil, Almond oil, Neem oil, Moringa oil, Borago oil, Olive oil, Peanuts oil, Hazelnuts oil, Walnut oil, Palm oil, Papaya seeds oil, Parsley seeds oil, Seabuckthorn oil, Castor oil, Rice oil, Sesame oil, Shea butter/karité butter, Sunflower oil, Soybean oil, Tamanu oil, Evening primrose oil, Grape seeds oil, Cranberry seeds oil.

In a most preferred embodiment of the present invention the component (b-2) of formula (III) is composed mainly of oleic, linoleic, and linolenic esterified on a glycerol molecule in various combinations.

Besides the present invention claims the use of acetophenone derivative of formula (I)

(I)

wherein
$R_1$ stands for hydrogen or methyl, and
$R_2$ stands for hydrogen, hydroxyl or a —$OCH_3$ group, or a cosmetically or pharmaceutically acceptable salt thereof,
for stabilizing the taste and/or odor of unsaturated fatty acid (esters).

Preferably, the acetophenone derivative of formula (I) are selected from the group consisting of

2-hydroxyacetophenone (Ia)

3-hydroxyacetophenone (Ib)

4-hydroxyacetophenone (Ic)

or their mixtures. More preferably the acetophenone derivative of formula (I) is 4-hydroxyacetophenone.

In a preferred embodiment the unsaturated fatty acids (esters) are mono- or polyunsaturated $C_8$-$C_{22}$ fatty acids or its monohydric or polyhydric $C_1$-$C_{18}$ aliphatic alcohols ester.

In a more preferred embodiment the mono- or polyunsaturated $C_8$-$C_{22}$ fatty acids or its monohydric or polyhydric $C_1$-$C_{18}$ aliphatic alcohols ester comprise:

(b-1) at least one acyl compound of formula (II)

(II)

wherein
R stands for hydrogen atom or an $C_1$-$C_{18}$ alkyl group and
X represents a mono- or polyunsaturated $C_8$-$C_{22}$ acyl group, and/or (b-2) at least one acylglycerol compound of formula (III)

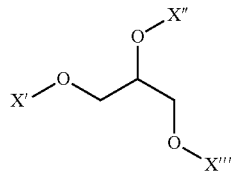
(III)

wherein
X', X" and X'" independently of one another represents a hydrogen atom or a saturated or mono- or polyunsaturated $C_8$-$C_{22}$ acyl group,
with the proviso that X', X" and X'" do not simultaneously represent hydrogen atom and at least one of X', X" and X'" being unsaturated acyl group.

In another preferred embodiment the used amount of acetophenone derivative of formula (I) is 0.01 to 5 wt. %, preferably in the range from 0.05 to 2 wt. %, and particularly preferably in the range from 0.1 to 1 wt. % relative to the total weight of the composition.

INDUSTRIAL APPLICATION

Personal Care Compositions

Another object of the present invention is to provide a personal care composition or a cosmetic composition, which comprise the composition with stabilized taste and/or odor according to the present invention.

The personal care or cosmetic compositions may contain abrasives, antiacne agents, agents against ageing of the skin, anticellulitis agents, antidandruff agents, antiinflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivativesand the like as additional auxiliaries and additives.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear saturated C6-C22-fatty acids with linear or branched C6-C22-fatty alcohols or esters of branched saturated C6-C13-carboxylic acids with linear or branched C6-C22-fatty alcohols, such as, for example, myristyl myristate, myristyl palmitate, myristyl stearate, myristyl isostearate, myristyl behenate, cetyl myristate, cetyl palmitate, cetyl stearate, cetyl isostearate, cetyl behenate, stearyl myristate, stearyl palmitate, stearyl stearate, stearyl isostearate, stearyl behenate, isostearyl myristate, isostearyl palmitate, isostearyl stearate, isostearyl isostearate, isostearyl behenate, oleyl myristate, oleyl palmitate, oleyl stearate, oleyl isostearate, oleyl behenate, behenyl myristate, behenyl palmitate, behenyl stearate, behenyl isostearate, behenyl behenate, erucyl myristate, erucyl palmitate, erucyl stearate, erucyl isostearate, erucyl behenate and. Also suitable are esters of saturated linear C6-C22-fatty acids with branched alcohols, in particular 2-ethylhexanol, esters of C18-C38-alkylhydroxy carboxylic acids with linear or branched C6-C22-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on saturated C6-C10-fatty acids, liquid mono-/di-/triglyceride mixtures based on saturated C6-C18-fatty acids, esters of C6-C22-fatty alcohols and/or Guerbet alcohols with aromatic carboxylic acids, in particular benzoic acid, esters of C2-C12-dicarboxylic acids with linear or branched alco-hols having 1 to 22 carbon atoms or polyols having 2 to 10 carbon atoms and 2 to 6 hydroxyl groups, branched primary alcohols, substituted cyclohexanes, linear and branched C6-C22-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched C6-C22-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol,
  polyalkylene glycols and
  glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl nnethacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consistiung of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
  p-aminobenzoic acid
  p-aminobenzoic acid ethyl ester (25 mol) ethoxylated (INCI name: PEG-25 PABA)
  p-dimethylaminobenzoic acid-2-ethylhexyl ester
  p-aminobenzoic acid ethyl ester (2 mol) N-propoxylated
  p-aminobenzoic acid glycerol ester
  salicylic acid homomenthyl ester (homosalates) (Neo Heliopan® HMS)
  salicylic acid-2-ethylhexyl ester (Neo Heliopan® OS)
  triethanolamine salicylate
  4-isopropyl benzyl salicylate
  anthranilic acid menthyl ester (Neo Heliopan® MA)
  diisopropyl cinnamic acid ethyl ester
  p-methoxycinnamic acid-2-ethylhexyl ester (Neo Heliopan® AV)
  diisopropyl cinnamic acid methyl ester
  p-methoxycinnamic acid isoamyl ester (Neo Heliopan® E 1000)
  p-methoxycinnamic acid diethanolamine salt
  p-methoxycinnamic acid isopropyl ester
  2-phenylbenzimidazole sulfonic acid and salts (Neo Heliopan® Hydro)
  3-(4'-trimethylammonium) benzylidene bornan-2-one methyl sulfate
  beta-imidazole-4(5)-acrylic acid (urocanic acid)
  3-(4'-sulfo)benzylidene bornan-2-one and salts
  3-(4'-methyl benzylidene)-D,L-camphor (Neo Heliopan® MBC)
  3-benzylidene-D,L-camphor
  N-[(2 and 4)-[2-(oxoborn-3-ylidene) methyl]benzyl]acrylamide polymer
  4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
  benzylidene malonate polysiloxane (Parsol® SLX)
  glyceryl ethylhexanoate dimethoxycinnamate
  dipropylene glycol salicylate
  tris(2-ethylhexyl)-4,4',4"-(1,3,5-triazine-2,4,6-triyltriimino)tribenzoate (=2,4,6-trianilino-(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
  2-ethylhexyl-2-cyano-3,3-diphenyl acrylate (Neo Heliopan® 303)
  ethyl-2-cyano-3,3'-diphenyl acrylate
  2-hydroxy-4-methoxybenzophenone (Neo Heliopan® BB)
  2-hydroxy-4-methoxybenzophenone-5-sulfonic acid
  dihydroxy-4-methoxybenzophenone
  2,4-dihydroxybenzophenone
  tetrahydroxybenzophenone
  2,2'-dihydroxy-4,4'-dimethoxybenzophenone
  2-hydroxy-4-n-octoxybenzophenone
  2-hydroxy-4-methoxy-4'-methyl benzophenone
  sodium hydroxymethoxybenzophenone sulfonate
  disodium-2,2'-dihydroxy-4,4'-dimethoxy-5,5'-disulfobenzophenone
  phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
  2,2'-methylene bis-(6-(2H-benzotriazol-2-yl)-4-1,1,3,3-tetramethylbutyl) phenol) (Tinosorb® M)
  2,4-bis-[4-(2-ethylhexyloxy)-2-hydroxyphenyl]-1,3,5-triazine
  2,4-bis-[{(4-(2-ethylhexyloxy)-2-hydroxy}phenyl]-6-(4-methoxyphenyl)-1,3,5-triazine (Tinosorb® S)
  2,4-bis-[{(4-(3-sulfonato)-2-hydroxypropyloxy)-2-hydroxy}phenyl]-6-(4-methoxyphenyl)-1,3,5-triazine sodium salt
  2,4-bis-[{(3-(2-propyloxy)-2-hydroxypropyloxy)-2-hydroxy}phenyl]-6-(4-methoxyphenyl)-1,3,5-triazine
  2,4-bis-[{4-(2-ethylhexyloxy)-2-hydroxy}phenyl]-6-[4-(2-methoxyethyl carbonyl) phenylamino]-1,3,5-triazine
  2,4-bis-[{4-(3-(2-propyloxy)-2-hydroxypropyloxy)-2-hydroxy}phenyl]-6-[4-(2-ethylcarboxyl) phenylamino]-1,3,5-triazine
  2,4-bis-[{4-(2-ethylhexyloxy)-2-hydroxy}phenyl]-6-(1-methylpyrrol-2-yl)-1,3,5-triazine
  2,4-bis-[{4-tris-(trimethylsiloxysilylpropyloxy)-2-hydroxy}phenyl]-6-(4-methoxyphenyl)-1,3,5-triazine 2,4-bis-[{4-(2''-methylpropenyloxy)-2-hydroxy}phenyl]-6-(4-methoxyphenyl)-1,3,5-triazine 2,4-bis-[{4-(1',1',1',3',5',5',5'-heptamethylsiloxy-2''-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of 4-isopropyl dibenzoyl methane terephthalylidene dibornane sulfonic acid and salts (Mexoryl® SX)

4-t-butyl-4'-methoxydibenzoyl methane (avobenzone)/(Neo Heliopan® 357)

phenylene bis-benzimidazyl tetrasulfonic acid disodium salt (Neo Heliopan® AP)

2,2'-(1,4-phenylene)-bis-(1H-benzimidazole-4,6-disulfonic acid), monosodium salt 2-(4-diethylamino-2-hydroxybenzoyl) benzoic acid hexyl ester (Uvinul® A Plus)

indanylidene compounds in accordance with DE 100 55 940 A1 (=WO 2002 038537 A1)

UV filters which are more preferably combined with one or more compounds of formula (I) in a preparation according to the present invention are selected from the group consisting of p-aminobenzoic acid 3-(4'-trimethylammonium) benzylidene bornan-2-one methyl sulfate salicylic acid homomenthyl ester (Neo Heliopan® HMS)

2-hydroxy-4-methoxybenzophenone (Neo Heliopan® BB)

2-phenylbenzimidazole sulfonic acid (Neo Heliopan® Hydro)

terephthalylidene dibornane sulfonic acid and salts (Mexoryl® SX)

4-tert-butyl-4'-methoxydibenzoyl methane (Neo Heliopan® 357)

3-(4'-sulfo)benzylidene bornan-2-one and salts 2-ethylhexyl-2-cyano-3,3-diphenyl acrylate (Neo Heliopan® 303)

N-[(2 and 4)-[2-(oxoborn-3-ylidene) methyl]benzyl]acrylamide polymer p-methoxycinnamic acid-2-ethylhexyl ester (Neo Heliopan® AV)

p-aminobenzoic acid ethyl ester (25 mol) ethoxylated (INCI name: PEG-25 PABA)

p-methoxycinnamic acid isoamyl ester (Neo Heliopan® E1000)

2,4,6-trianilino-(p-carbo-2'-ethylhexyl-1'-oxy)-1,3,5-triazine (Uvinul® T150)

phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan® MBC)

3-benzylidene camphor salicylic acid-2-ethylhexyl ester (Neo Heliopan® OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb® M)

phenylene bis-benzimidazyl tetrasulfonic acid disodium salt (Neo Heliopan® AP)

2,4-bis-[{(4-(2-ethylhexyloxy)-2-hydroxy}phenyl]-6-(4-methoxyphenyl)-1,3,5-triazine (Tinosorb® S)

benzylidene malonate polysiloxane (Parsol® SLX)

menthyl anthranilate (Neo Heliopan® MA)

2-(4-diethylamino-2-hydroxybenzoyl) benzoic acid hexyl ester (Uvinul® A Plus)

indanylidene compounds in accordance with DE 100 55 940 (=WO 02/38537).

Secondary Sun Protection Factors

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Anti-Ageing Actives

In the context of the invention, anti-ageing or biogenic agents are, for example antioxidants, matrix-metalloproteinase inhibitrors (MMPI), skin moisturizing agents, glycosaminglycan stimulkators, anti-inflammatory agents, TRPV1 antagonists and plant extracts.

Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, Rubus Fruticosus (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, Arctium lappa fruit extract, Eriobotrya japonica extract, Genkwanin, N-Methyl-L-serine, (−)-alpha-bisabolol or synthetic alpha-bisabolol such as e.g. Dragosantol and Dragosantol 100 from Symrise, oat glucan, Echinacea purpurea extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, Echinacea purpurea extract, Sinorhizobium Meliloti Ferment Filtrate, Calcium ketogluconate, Alpinia galanga leaf extract and tetradecyl aminobutyroylvalylaminobutyric urea trifluoroacetate.

Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, Passiflora incarnata, witch hazel, ginger or Echinacea; preferably selected from the group consisting of extracts or fractions from camomile, Aloe vera, oats, calendula, arnica, honeysuckle, rosemary, witch hazel, ginger or Echinacea, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the µ-receptor, e.g. acetyl tetrapeptide-15, are preferred.

Botanical extracts. The compositions may also contain various extracts of plants, such as for example extracts of *Ginkgo biloba, Oleacea europensis, Glyzyrrhiza glabra, Vacciniurn myrtillus, Trifolium pratense, Litchi sinensis, Vitis, vinifera, Brassica oleracea, Punica granatum, Petroselinium crispum, Centella asiatica, Passiflora incarnata, Medicago sativa, Melissa officinalis, Valeriana officinalis, Castanea sativa, Salix alba* and *Hapagophytum procumbens.*

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, l-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3]or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, l-(−)- isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)-N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4- hydroxybenzoic acid and its salts and esters, N-(4-chlorophenyl)-N'-(3,4- dichlorophenyl)urea, 2,4,4'-trichloro-2'-hydroxy-diphenyl ether (triclosan), 4-chloro-3,5-dimethyl-phenol, 2,2'-methylenebis(6-bromo-4- chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2- propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-yl methyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are
  glycerol;
  alkylene glycols such as, for example, ethylene glycol, diethylene glycol, propylene glycol, butylene glycol, hexylene glycol and polyethylene glycols with an average molecular weight of 100 to 1000 Dalton;
  technical oligoglycerol mixtures with a degree of self-condensation of 1.5 to 10, such as for example technical diglycerol mixtures with a diglycerol content of 40 to 50% by weight;
  methylol compounds such as, in particular, trimethylol ethane, trimethylol propane, trimethylol butane, pentaerythritol and dipentaerythritol;
  lower alkyl glucosides, particularly those containing 1 to 8 carbon atoms in the alkyl group, for example methyl and butyl glucoside;
  sugar alcohols containing 5 to 12 carbon atoms, for example sorbitol or mannitol,
  sugars containing 5 to 12 carbon atoms, for example glucose or sucrose;
  amino sugars, for example glucamine;
  dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ?- -isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C. I. 16255), patent blue V (C. I. 42051), indigotin (C. I. 73015), chlorophyllin (C. I. 75810), quinoline yellow (C. I. 47005), titanium dioxide (C. I. 77891), indanthrene blue RS (C. I. 69800) and madder lake (C. I. 58000). Luminol may also be present as a luminescent dye. Advantageous coloured pigments are for example titanium dioxide, mica, iron oxides (e.g. $Fe_2O_3Fe_3O_4$, FeO(OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b. w., preferably 10 to 80% b. w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b. w., preferably 5 to 80% b. w., based on the total weight of the preparation.

Food Compositions

Another object of the present invention is to provide food compositions, which comprise the composition with stabilized taste and/or odor according to the present invention.

Food compositions according to the invention are any preparations or compositions which are suitable for consumption and are used for nutrition or enjoyment purposes, and are generally products which are intended to be introduced into the human or animal oral cavity, to remain there for a certain time and then either be eaten (e.g. ready-to-eat foodstuffs or feeds, see also herein below) or removed from the oral cavity again (e.g. chewing gums). Such products include any substances or products which in the processed, partially processed or unprocessed state are to be ingested by humans or animals. They also include substances which are added to orally consumable products during their manufacture, preparation or treatment and which are intended to be introduced into the human or animal oral cavity.

The food compositions according to the invention also include substances which in the unchanged, treated or prepared state are to be swallowed by a human or animal and then digested; in this respect, the orally consumable products according to the invention also include casings, coatings or other encapsulations which are to be swallowed at the same time or which may be expected to be swallowed. The expression "orally consumable product" covers ready-to-eat foodstuffs and feeds, that is to say foodstuffs or feeds that are already complete in terms of the substances that are important for the taste. The expressions "ready-to-eat foodstuff" and "ready-to-eat feed" also include drinks as well as solid or semi-solid ready-to-eat foodstuffs or feeds. Examples which may be mentioned are frozen products, which must be thawed and heated to eating temperature before they are eaten. Products such as yoghurt or ice-cream as well as chewing gums or hard caramels are also included among the ready-to-eat foodstuffs or feeds.

Preferred food compositions according to the invention also include "semi-finished products". Within the context of the present text, a semi-finished product is to be understood as being an orally consumable product which, because of a very high content of flavourings and taste-imparting substances, is unsuitable for use as a ready-to-eat orally consumable product (in particular foodstuff or feed). Only by mixing with at least one further constituent (e.g. by reducing the concentration of the flavourings and taste-imparting substances in question) and optionally further process steps (e.g. heating, freezing) is the semi-finished product converted into a ready-to-eat orally consumable product (in particular foodstuff or feed). Examples of semi-finished products which may be mentioned here are Food composition according to the invention preferably comprises one or more preparations for nutrition or enjoyment purposes. These include in particular (reduced-calorie) baked goods (e.g. bread, dry biscuits, cakes, other baked articles), confectionery (e.g. chocolates, chocolate bars, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshing drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, precooked ready-to-eat rice products), dairy products (e.g. full-fat or reduced-fat or fat-free milk drinks, rice pudding, yoghurt, kefir, cream cheese, soft cheese, hard cheese, dried milk powder, whey, butter, buttermilk, partially or completely hydrolysed milk-protein-containing products), products made from soy protein or other soybean fractions (e.g. soy milk and products produced therefrom, drinks containing isolated or enzymatically treated soy protein, drinks containing soy flour, preparations containing soy lecithin, fermented products such as tofu or tempeh or products produced therefrom and mixtures with fruit preparations and optionally flavours), fruit preparations (e.g. jams, sorbets, fruit sauces, fruit fillings), vegetable preparations (e.g. ketchup, sauces, dried vegetables, frozen vegetables, precooked vegetables, boiled-down vegetables), snacks (e.g. baked or fried potato crisps or potato dough products, maize- or groundnut-based extrudates), fat- and oil-based products or emulsions thereof (e.g. mayonnaise, remoulade, dressings, in each case full-fat or reduced-fat), other ready-made dishes and soups (e.g. dried soups, instant soups, precooked soups), spices, spice mixtures and in particular seasonings which are used, for example, in the snacks field, sweetener preparations, tablets or sachets, other preparations for sweetening or whitening drinks or other foods. The preparations within the scope of the invention can also be used in the form of semi-finished products for the production of further preparations for nutrition or enjoyment purposes. The preparations within the scope of the invention can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, and in the form of food supplements.

The preparations can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, for example in the form of food supplements.

The semi-finished products are generally used for the production of ready-to-use or ready-to-eat preparations for nutrition or enjoyment purposes.

Further constituents of a ready-to-eat preparation or semi-finished product for nutrition or enjoyment purposes can be conventional base substances, auxiliary substances and additives for foods or enjoyment foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices, vegetable pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, cocoa fat, hardened vegetable fat), oils (e.g. sunflower oil, groundnut oil, maize germ oil, olive oil, fish oil, soya oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste correctors for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxy-propionic acid), emulsifiers (e.g. lecithins, diacylglycerols, gum arabic), stabilisers (e.g. carrageenan, alginate), preservatives (e.g. benzoic acid and its salts, sorbic acid and its salts), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonene, amarogentine, humulone, lupulone, catechols, tannins), substances that prevent enzymatic browning (e.g. sulfite, ascorbic acid), ethereal oils, plant extracts, natural or synthetic colourings or colouring pigments (e.g. carotinoids, flavonoids, anthocyans, chlorophyll and derivatives thereof), spices, trigeminally active substances or plant extracts containing such trigeminally active substances, synthetic, natural or nature-identical flavourings or odorants as well as odour correctors.

Food compositions according to the invention, for example those in the form of preparations or semi-finished products, preferably comprise a flavour composition in order to complete and refine the taste and/or odour. A preparation can comprise as constituents a solid carrier and a flavour composition. Suitable flavour compositions comprise, for example, synthetic, natural or nature-identical flavourings, odorants and taste-imparting substances, reaction flavourings, smoke flavourings or other flavour-giving preparations (e.g. protein (partial) hydrolysates, preferably protein (partial) hydrolysates having a high arginine content, barbecue flavourings, plant extracts, spices, spice preparations, vegetables and/or vegetable preparations) as well as suitable auxiliary substances and carriers. Particularly suitable here are the flavour compositions or constituents thereof which produce a roasted, meaty (in particular chicken, fish, seafood, beef, pork, lamb, mutton, goat), vegetable-like (in particular tomato, onion, garlic, celery, leek, mushroom, aubergine, seaweed), spicy (in particular black and white pepper, cardamom, nutmeg, pimento, mustard and mustard products), fried, yeast-like, boiled, fatty, salty and/or pungent flavour impression and accordingly can enhance the spicy impression. The flavour compositions generally comprise more than one of the mentioned ingredients.

The food compositions of the present invention are preferably selected from the group comprising confectionery, preferably reduced-calorie or calorie-free confectionery, preferably selected from the group comprising muesli bar products, fruit gums, dragées, hard caramels and chewing gum, non-alcoholic drinks, preferably selected from the group comprising green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit and vegetable juice preparations, instant drinks, preferably selected from the group comprising instant (green, black, rooibos, herbal) tea drinks, cereal products, preferably selected from the group comprising low-sugar and sugar-free breakfast cereals and muesli bars, dairy products, preferably selected from the group comprising reduced-fat and fat-free milk drinks, yoghurt, kefir, whey, buttermilk and ice-cream, products made from soy protein or other soybean fractions, preferably selected from the group comprising soy milk, products produced from soy milk, drinks containing isolated or enzymatically treated soy protein, drinks containing soy flour, preparations containing soy lecithin, products produced from preparations containing soy lecithin and mixtures with fruit preparations and optionally flavours, sweetener preparations, tablets and sachets, sugar-free dragées, ice-cream, with or without milk-based constituents, preferably sugar-free.

Aroma or Flavouring Compounds

Aroma compounds and flavouring agents (component d) are well known in the art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as eucalyptus, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, linnonene (preferably D-linnonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, eucalyptus oil, thyme oil, cinnamon oil, clove oil, spruce needle oil, fennel oil, sage oil, aniseed oil, star anise oil, chamomile oil, and caraway oil, and their mixtures.

Sweeteners

The term "sweeteners" here denotes substances having a relative sweetening power of at least 25, based on the sweetening power of sucrose (which accordingly has a sweetening power of 1). Sweeteners to be used in an orally consumable product (in particular foodstuff, feed or medicament) according to the invention (a) are preferably non-cariogenic and/or have an energy content of not more than 5 kcal per gram of the orally consumable product.

Advantageous sweeteners in a preferred food composition according to the invention are selected from the following groups:

Naturally occurring sweeteners, preferably selected from the group comprising
miraculin, monellin, mabinlin, thaumatin, curculin, brazzein, pentaidin, D-phenylalanine, D-tryptophan, and extracts or fractions obtained from natural sources, comprising those amino acids and/or proteins, and the physiologically acceptable salts of those amino acids and/or proteins, in particular the sodium, potassium, calcium or ammonium salts;

neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin 3-acetate, perillartin, telosmoside $A_{15}$, periandrin I-V, pterocaryosides, cyclocaryosides, mukuroziocides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizine, and the physiologically acceptable salts of those compounds, in particular the sodium, potassium, calcium or ammonium salts;

extracts or concentrated fractions of the extracts, selected from the group comprising thaumatococcus extracts (katamfe plant), extracts from *Stevia* ssp. (in particular *Stevia rebaudiana*), swingle extracts (*Momordica* or *Siratia grosvenorii*, Luo-Han-Guo), extracts from *Glycerrhyzia* ssp. (in particular *Glycerrhyzia glabra*), extracts from *Rubus* ssp. (in particular *Rubus suavissimus*), citrus extracts and extracts from *Lippia dulcis;*

Synthetic sweet-tasting substances, preferably selected from the group comprising magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

Thickeners

Advantageous thickeners in a preferred orally consumable product (in particular foodstuff, feed or medicament) according to the invention are selected from the group comprising: crosslinked polyacrylic acids and derivatives thereof, polysaccharides and derivatives thereof, such as xanthan gum, agar-agar, alginates or tyloses, cellulose derivatives, for example carboxymethylcellulose or hydroxycarboxymethylcellulose, fatty alcohols, monoglycerides and fatty acids, polyvinyl alcohol and polyvinylpyrrolidone.

Preference is given according to the invention to an orally consumable product (in particular foodstuff or feed) which comprises milk thickened with lactic acid bacteria and/or cream thickened with lactic acid bacteria and which preferably is selected from the group comprising yoghurt, kefir and quark.

A food composition according to the invention comprising milk thickened with lactic acid bacteria and/or cream thickened with lactic acid bacteria is advantageously an orally consumable product which comprises a probiotic, wherein the probiotic is preferably selected from the group comprising *Bifidobacterium animalis* subsp. lactis BB-12,

*Bifidobacterium animalis* subsp. lactis DN-173 010, *Bifidobacterium animalis* subsp. lactis HN019, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus* reuteri (ATCC 55730) and *Lactobacillus rhamnosus* (ATCC 53013).

Additives for Chewing Gums

Particular preference is given to an orally consumable product (in particular foodstuff, feed or medicament) according to the invention that is a chewing gum and comprises a chewing-gum base. The chewing-gum base is preferably selected from the group comprising chewing-gum or bubble-gum bases. The latter are softer, so that gum bubbles can also be formed therewith. Preferred chewing-gum bases according to the invention include, in addition to the natural resins or the natural latex chicle that are traditionally used, elastomers such as polyvinyl acetate (PVA), polyethylene, (low or medium molecular weight) polyisobutene (PIB), polybutadiene, isobutene-isoprene copolymers (butyl rubber), polyvinylethyl ether (PVE), polyvinylbutyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or 6,986,709. In addition, chewing-gum bases that are preferably to be used according to the invention preferably comprise further constituents such as, for example, (mineral) fillers, plasticisers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminium oxide, dicalcium phosphate, tricalcium phosphate, magnesium hydroxide and mixtures thereof. Suitable plasticisers, or agents for preventing adhesion (detackifiers), are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides such as lecithin, mono- and di-glycerides of fatty acids, for example glycerol monostearate.

Chewing gums according to the invention (in particular as disclosed above) preferably comprise constituents such as sugars of different types, sugar substitutes, other sweet-tasting substances, sugar alcohols (in particular sorbitol, xylitol, mannitol), ingredients having a cooling effect, taste correctors for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilisers, odour correctors and flavours (e.g. eucalyptus-menthol, cherry, strawberry, grapefruit, vanilla, banana, citrus, peach, blackcurrant, tropical fruits, ginger, coffee, cinnamon, combinations (of the mentioned flavours) with mint flavours as well as spearmint and peppermint on their own). The combination inter alia of the flavours with further substances that have cooling, warming and/or mouth-watering properties is of particular interest.

Methods for Stabilizing the Taste and/or Odor of Fatty Acid (Esters)

Another object of the present invention is to provide a method for stabilizing the taste and/or odor of unsaturated fatty acids (esters), whereby acetophenone derivative of formula (I)

wherein $R_1$ stands for hydrogen or methyl, and $R_2$ stands for hydrogen, hydroxyl or a —$OCH_3$ group, or a cosmetically or pharmaceutically acceptable salt thereof, is added into the unsaturated fatty acids (esters).

Preferably, the acetophenone derivative of formula (I) are selected from the group consisting of

2-hydroxyacetophenone

3-hydroxyacetophenone

4-hydroxyacetophenone or their mixtures. More preferably the acetophenone derivative of formula (I) is 4-hydroxyacetophenone.

In a preferred embodiment the unsaturated fatty acids (esters) are mono- or polyunsaturated $C_8$-$C_{22}$ fatty acids or its monohydric or polyhydric $C_1$-$C_{18}$ aliphatic alcohols ester.

In a more preferred embodiment the mono- or polyunsaturated $C_8$-$C_{22}$ fatty acids or its monohydric or polyhydric $C_1$-$C_{18}$ aliphatic alcohols ester comprise:

(b-1) at least one acyl compound of formula (II)

(II)

wherein

R stands for hydrogen atom or an $C_1$-$C_{18}$ alkyl group and

X represents a mono- or polyunsaturated $C_8$-$C_{22}$ acyl group, and/or (b-2) at least one acylglycerol compound of formula (III)

(III)

wherein

X', X" and X'" independently of one another represents a hydrogen atom or a saturated or mono- or polyunsaturated $C_8$-$C_{22}$ acyl group, with the proviso that X', X" and X'" do not simultaneously represent hydrogen atom and at least one of X', X" and X'" being unsaturated acyl group.

In a another preferred embodiment the added amount of acetophenone derivative of formula (I) is in the range from about 0.01 to 5 wt. %, preferably in the range from 0.05 to 2 wt. %, and particularly preferably in the range from 0.1 to 1 wt. % relative to the total weight of the composition.

The inhibition of the radical formation of the test substance is calculated by the following formula:

$$\text{Inhibition [\%]} = 100 - \left(\frac{A_{test\ substance}}{A_{control}} \times 100\right)$$

Wherein the abbreviations have the following meanings:

$A_{test\ substance}$: Absorption of the wells with test substance including 4-hydroxyacetophenone and alpha-tocopherol $A_{control}$: Absorption of the wells without test substance From the inhibition of the radical formation [%] in a series of dilutions of tested samples the $IC_{50}$ was calculated. This is the concentration at which the radical formation is inhibited by 50%. The results are shown in Table 1:

TABLE 1

| Activity based on the inhibition of radical formation (mean value from at least 2 independent tests) | |
|---|---|
| Test Substance | $IC_{50}$ (µM) |
| 4-hydroxyacetophenone | 262.3 |
| alpha-tocopherol | 26.8 |

The results show that 4-hydroxyacetophenone exhibits a 10 fold higher $IC_{50}$ value than alpha-tocopherol. That means 4-hydroxyacetophenone with a concentration of 262.3 µM can inhibit 50% of the radical formation, whereas only 26.8 µM of alpha-tocopherol were required to do the same. Therefore 4-hydroxyacetophenone has much weaker antioxidant activity compared with alpha-tocopherol.

Example 2

Stabilization of Argan Oil

To evaluate the odor protecting effect of Hydroxyacetophenone on oils, oil samples comprising Argan oil without (A) and with different additives (B to E) were prepared as given in Table 2.

TABLE 2

| The composition of oil samples A to E (amounts in % b.w.) | | | | | | |
|---|---|---|---|---|---|---|
| Ingredient | INCI Name | A | B | C | D | E |
| Argan oil | *Argania Spinosa* Kernel Oil | Ad 100 | Ad 100 | Ad 100 | Ad 100 | Ad 100 |
| Alpha-Tocopherol | Tocopherol | \ | 0.5 | \ | \ | \ |
| Tocopheryl acetate | Tocopheryl acetate | \ | \ | 0.5 | \ | \ |
| Covi-Ox T 70C (blend of tocopherols) | Tocopherol | \ | \ | \ | 0.5 | \ |
| 4-Hydroxyacetophenone | Hydroxyacetophenone | \ | \ | \ | \ | 0.5 |

EXAMPLES

Example 1

Evaluation of Anti-Oxidant Activity

By means of the ABTS-assay the anti-oxidative capacity of 4-hydroxyacetophenone and alpha-tocopherol was compared. 2,2'-azino bis-(3-ethylbenzothiazoline 6-sulfonic acid) (ABTS) was transformed by potassium persulfate into the blue-green radical cation ABTS•+. Through the addition of 4-hydroxyacetophenone and alpha-tocopherol the radical cations were reduced and discoloration was observed, which was determined photometrically by Absorption at 734 nm.

Generally argan oil (INCI: Argania Spinosa Kernel Oil) is a clear, yellow to orange liquid characterized by acylglycerols containing 42-50% oleic acid (C18:1), 30-36% linoleic acid, 12-16% palmitic acid (C16:0), and 4-6% stearic acid (C18:0). It has a very characteristic and strong odour.

In this experiment the Argan oil quality used was characterized by acylglycerol compounds containing 51% oleic acid (C18:1), 35% linoleic acid, 14% palmitic acid (C16:0), and 6% stearic acid (C18:0) as determined by GC analysis after methanolysis via the respective fatty acid methyl esters. Furthermore, it contained 0.29% oleic acid (C18:1) and 0.25% linoleic acid as free fatty acids as determined by HPLC analysis with light scattering detection and diode array detection, respectively.

Acyl and acylglycerol compounds were characterized by HPLC-MS and listed in Table 3: HPLC-MS: YMC ODS-AQ, 5 μm, 150×3 mm with pre-column, temperature: 40° C., flow: 0.4 ml/min, gradient from 100% methanol to 100% isopropanol, detection wavelength 205 nm, after column addition of a 100 mM methanolic ammonium formiate solution by syringe pump, flow: 0.150 μl/h, MS ion trap, ESI in positive and negative ion mode with Auto MS/MS fragmentation, scan 200 to 1500.

TABLE 3

Characterization of acyl and acylglycerol compounds by HPLC-MS measurement in negative (investigation of free fatty acids) and positive (investigation of acylglycerol compounds) ion mode

| Retention time in min | ESI neg. m/z | ESI pos m/z | Molecular weight M | Compound |
|---|---|---|---|---|
| 3.2 | 279 (1) | | 280 | Linoleic acid |
| 3.5 | 255 (1) | | 256 | Palmitic acid |
| 3.6 | 281 (1) | | 282 | Oleic acid |
| 4.1 | 283 (1) | | 284 | Stearic acid |
| 2.9 | | 377 (3) | 354 | L Monoacylglycerol |
| 3.2 | | 379 (3) | 356 | O Monoacylglycerol |
| 6.7 | | 639 (2) | 621 | LS Diacylgylcerol |
| 6.9 | | 635 (2) | 617 | LL Diacylgylcerol |
| 7.3 | | 615 (2) | 597 | PS Diacylgylcerol |
| 7.4 | | 611 (2) | 593 | LP Diacylgylcerol |
| 7.7 | | 637 (2) | 619 | OL Diacylgylcerol |
| 7.7 | | 641 (2) | 623 | OS Diacylgylcerol |
| 8.4 | | 613 (2) | 595 | OP Diacylgylcerol |
| 8.5 | | 639 (2) | 621 | OO Diacylgylcerol |
| 14.4 | | 897 (2) | 879 | LLL Triacylglycerol |
| 15.2 | | 873 (2) | 855 | LLP Triacylglycerol |
| 15.3 | | 899 (2) | 881 | LLO Triacylglycerol |
| 15.6 | | 825 (2) | 807 | PPP Triacylglycerol |
| 15.7 | | 849 (2) | 831 | PPL Triacylglycerol |
| 15.9 | | 875 (2) | 857 | OLP Triacylglycerol |
| 16.2 | | 901 (2) | 883 | LLS Triacylglycerol |
| 16.2 | | 901 (2) | 883 | OOL Triacylglycerol |
| 16.5 | | 851 (2) | 833 | PPO Triacylglycerol |
| 16.6 | | 877 (2) | 859 | OOP Triacylglycerol |
| 16.9 | | 903 (2) | 885 | OOO Triacylglycerol |
| 17.5 | | 881 (2) | 863 | SSP Triacylglycerol |
| 17.5 | | 879 (2) | 861 | OPS Triacylglycerol |
| 17.6 | | 905 (2) | 887 | OOS Triacylglycerol |

(1) M − 1 for the [M − H]$^-$ ion
(2) M + 18 for the [M + NH$_4$]$^+$ ion
(3) M + 23 for the [M + Na]$^+$ ion
In the table acyl radicals are abbreviated as follows:
O = oleic acid, L = linoleic acid, P = palmitic acid, and S = stearic acid.

The oil samples were divided respectively into 3 portions each and the portions were stored for 1 and 2 months either at room temperature exposed to normal daylight (RTL) or at 40° C. or 50° C. in a heating cabinet, respectively. After the treatments, the absorbance at 232 nm was determined as this correlates with the state of oxidation by detecting conjugated dienes as specific oxidized compounds. Modulation versus start t=0 was calculated by the following formula and listed in Table 4:

$$\text{Modulation [\%]} = \left( \frac{\text{Absorbance after treatment} - \text{Absorbance at } t = 0}{\text{Absorbance at } t = 0} \times 100 \right)$$

TABLE 4

Absorbance at 232 nm and Modulation versus t = 0

|  | A | B | C | D | E |
|---|---|---|---|---|---|
| Absorbance at 232 nm | | | | | |
| Start t = 0 | 0.1581 | 0.2655 | 0.2101 | 0.2149 | 0.2590 |
| RTL, 1 month | 0.4993 | 0.8717 | 0.4422 | 0.5530 | 0.5260 |
| RTL, 2 months | 0.9468 | 1.9003 | 0.9839 | 1.1014 | 1.2119 |
| 40° C., 1 month | 0.2100 | 0.9206 | 0.2885 | 0.3747 | 0.3467 |
| 40° C., 2 months | 0.3195 | 1.9008 | 0.4536 | 0.6761 | 0.4352 |
| 50° C., 1 month | 0.3749 | 0.8642 | 0.4640 | 0.7117 | 0.4860 |
| 50° C., 2 months | 0.8220 | 3.9160 | 0.9593 | 1.7329 | 0.8895 |
| Modulation versus t = 0 [%] | | | | | |
| RTL, 1 month | 216 | 228 | 110 | 157 | 103 |
| RTL, 2 months | 499 | 616 | 368 | 413 | 368 |
| 40° C., 1 month | 33 | 247 | 37 | 74 | 34 |
| 40° C., 2 months | 102 | 616 | 116 | 215 | 68 |
| 50° C., 1 month | 137 | 225 | 121 | 231 | 88 |
| 50° C., 2 months | 420 | 1375 | 357 | 706 | 243 |

As can be seen from the able, 0.5% of 4-hydroxyacetophenone (sample E) leads to a lower increase of absorbance at 232 nm compared to sample A (Argan oil without additive) after 1 and 2 months. The protective effect of 4-hydroxyacetophenone was observed at all 3 treatments. 0.5% 4-hydroxyacetophenone (sample E) exhibited a better protection than 0.5% alpha-tocopherol (sample B), 0.5% tocopheryl acetate (sample C) and 0.5% Covi-Ox T 70C which is a blend of tocopherols (sample D).

Example 3

Stabilization of Avocado Oil

To evaluate the odour protecting effect of Hydroxyacetophenone on oils, oil samples comprising avocado oil without (A) and with different additives (B to D) were prepared as given in Table 5.

TABLE 5

The composition of oil samples A to D (amounts in % b.w.)

| Ingredient | INCI Name | A | B | C | D |
|---|---|---|---|---|---|
| Avocado oil | Persea Gratissima Oil | Ad 100 | Ad 100 | Ad 100 | Ad 100 |
| Alpha-Tocopherol | Tocopherol | \ | 0.5 | \ | \ |
| Tocopheryl Acetate | Tocopheryl Acetate | \ | \ | 0.5 | \ |
| 4-Hydroxy-acetophenone | Hydroxyacetophenone | \ | \ | \ | 0.5 |

Generally avocado oil (INCI: Persea Gratissima Oil) is clear or cloudy, colorless to yellow-green liquid characterized by acylglycerols containing about 65% oleic acid (C18:1) and 6-10% linoleic acid (C18:2) (Ölpflanzen-Pflanzenöle, L. Roth and K. Kormann ecomed 2000, page 117).

The avocado oil quality used in this experiment was characterized by acylglycerols containing 63% oleic acid (C18:1), 21% palmitic acid (C16:0), 11% linoleic acid, and 10% palmitoleic acid (C16:1) as determined by GC analysis after methanolysis via the respective fatty acid methyl esters.

Acyl and acylglycerol compounds were characterized by HPLC-MS and listed in Table 6: HPLC-MS: YMC ODS-AQ, 5 μm, 150×3 mm with pre-column, temperature: 40° C., flow: 0.4 ml/min, gradient from 100% methanol to 100% isopropanol, detection wavelength 205 nm, after column addition of a 100 mM methanolic ammonium formiate solution by syringe pump, flow: 0.150 μl/h, MS ion trap, ESI in positive and negative ion mode with Auto MS/MS fragmentation, Scan 200 to 1500.

TABLE 6

Characterization of acyl and acylglycerol compounds by HPLC-MS measurement in negative (investigation of free fatty acids) and positive (investigation of acylglycerol compounds) ion mode

| Retention time in min | ESI neg. m/z | ESI pos m/z | Molecular weight M | Compound |
|---|---|---|---|---|
| 3.2 | 253 (1) | | 254 | Palmitoleic acid |
| 3.3 | 279 (1) | | 280 | Linoleic acid |
| 3.5 | 255 (1) | | 256 | Palmitic acid |
| 3.6 | 281 (1) | | 282 | Oleic acid |
| 2.9 | | 377 (3) | 354 | L Monoacylglycerol |
| 3.0 | | 353 (3) | 330 | P Monoacylglycerol |
| 3.2 | | 379 (3) | 356 | O Monoacylglycerol |
| 6.2 | | 587 (2) | 569 | PP Diacylgylcerol |
| 6.3 | | 583 (2) | 565 | pp Diacylgylcerol |

TABLE 6-continued

Characterization of acyl and acylglycerol compounds by HPLC-MS measurement in negative (investigation of free fatty acids) and positive (investigation of acylglycerol compounds) ion mode

| Retention time in min | ESI neg. m/z | ESI pos m/z | Molecular weight M | Compound |
|---|---|---|---|---|
| 6.5 | | 609 (2) | 591 | Lp Diacylgylcerol |
| 6.8 | | 635 (2) | 617 | LL Diacylgylcerol |
| 7.3 | | 585 | 567 | Pp Diacylgylcerol |
| 7.4 | | 611 (2) | 593 | LP Diacylgylcerol |
| 7.7 | | 637 (2) | 619 | OL Diacylgylcerol |
| 8.2 | | 613 (2) | 613 | OP Diacylgylcerol |
| 8.5 | | 639 (2) | 621 | OO Diacylgylcerol |
| 13.7 | | 819 (2) | 801 | ppp Triacylglycerol |
| 14.0 | | 845 (2) | 827 | Lpp Triacylglycerol |
| 14.3 | | 871 (2) | 853 | LLp Triacylglycerol |
| 14.5 | | 897 (2) | 879 | LLL Triacylglycerol |
| 14.7 | | 821 (2) | 803 | Ppp Triacylglycerol |
| 15.1 | | 873 (2) | 855 | LLP Triacylglycerol |
| 15.3 | | 899 (2) | 881 | LLO Triacylglycerol |
| 15.7 | | 849 (2) | 831 | PPL Triacylglycerol |
| 15.9 | | 875 (2) | 857 | OOp Triacylglycerol |
| 16.1 | | 901 (2) | 883 | OOL Triacylglycerol |
| 16.5 | | 851 (2) | 833 | PPO Triacylglycerol |
| 16.7 | | 877 (2) | 859 | OOP Triacylglycerol |
| 17.0 | | 903 (2) | 885 | OOO Triacylglycerol |

(1) M − 1 for the [M − H]$^-$ ion
(2) M + 18 for the [M + NH$_4$]$^+$ ion
(3) M + 23 for the [M + Na]$^+$ ion
In the table acyl radicals are abbreviated as follows:
O = oleic acid, L = linoleic acid, P = palmitic acid, and p = palmitoleic acid.

The oil samples were divided into 3 portions each and the portions were stored for 1 and 2 months either at room temperature exposed to normal daylight (RTL) or at 40° C. or 50° C. in a heating cabinet, respectively. After the treatments, the absorbance at 232 nm was determined as this correlates with the state of oxidation by detecting conjugated dienes as specific oxidized compounds. Modulation versus start t=0 was calculated by the following formula and listed in Table 7:

$$\text{Modulation [\%]} = \left( \frac{\text{Absorbance after treatment} - \text{Absorbance at } t = 0}{\text{Absorbance at } t = 0} \times 100 \right)$$

TABLE 7

Absorbance at 232 nm and Modulation versus t = 0

| | A | B | C | D |
|---|---|---|---|---|
| Absorbance at 232 nm | | | | |
| Start t = 0 | 0.4630 | 0.5207 | 0.5912 | 0.5773 |
| RTL, 1 month | 0.9078 | 0.9457 | 0.7728 | 0.8978 |
| RTL, 2 months | 1.3464 | 1.5038 | 1.4112 | 1.3557 |
| 40° C., 1 month | 0.8092 | 0.9207 | 0.7990 | 0.9151 |
| 40° C., 2 months | 1.1648 | 1.4635 | 1.5189 | 1.3776 |
| 50° C., 1 month | 0.7653 | 1.0706 | 1.3888 | 0.8311 |
| 50° C., 2 months | 1.1082 | 1.8845 | 1.5483 | 1.1739 |
| Modulation versus t = 0 [%] | | | | |
| RTL, 1 month | 96 | 82 | 31 | 56 |
| RTL, 2 months | 191 | 189 | 139 | 135 |
| 40° C., 1 month | 75 | 77 | 35 | 59 |
| 40° C., 2 months | 152 | 181 | 157 | 139 |
| 50° C., 1 month | 65 | 106 | 135 | 44 |
| 50° C., 2 months | 139 | 262 | 162 | 103 |

As can be seen from the table, 0.5% of 4-hydroxyacetophenone (sample D) leads to a lower increase of absorbance at 232 nm compared to avocado oil without additive (A). The protective effect of 0.5% of 4-hydroxyacetophenone was observed at all 3 treatments. 0.5% of 4-hydroxyacetophenone (D) exhibited a better protection than 0.5% alpha-tocopherol (sample B) and 0.5% tocopheryl acetate (sample C).

Example 4

Olfactory Evaluation of a Crème Gel for Face Care Rich in Linoleic Acid

Two crème gels rich in linoleic acid with the compositions listed in Table 8 was prepared according to the following instructions:
(1) Firstly blending ingredients of phase A and phase B respectively,
(2) Dispersing ingredients of phase C into the mixture of phase B and further adding ingredients of phase A under high shear,
(3) Finally adding phase D under high shear into the mixture of phase A, B and C.
The pH values of the obtained two crème gel samples are both 6.

TABLE 8

The Composition of crème gels A and B (amounts in % b.w.)

| Phase | Ingredient | INCI Name | Gel A | Gel B |
|---|---|---|---|---|
| A | Water | Aqua | Ad 100 | Ad 100 |
|  | Glycerin | Glycerin | 3.0 | 3.0 |
| B | Dracorin GOC | Glyceryl Oleate Citrate Caprylic/Capric Triglyceride | 0.3 | 0.3 |
|  | Linoleic acid | Linoleic acid | 12.0 | 12.0 |
|  | Shea Butter | *Butyrospermum Parkii* Butter | 2.0 | 2.0 |
|  | 4-Hydroxy-acetophenone | Hydroxyacetophenone | 0.5 | \ |
| C | Cosmedia SP | Sodium Polyacrylate | 1.2 | 1.2 |
| D | SymOcide PS | Phenoxyethanol, Decylene Glycol, 1,2-Hexanediol | 1.0 | 1.0 |
| E | Tapioca Pure | Tapioca Starch | 1.0 | 1.0 |
|  | Total= |  | 100 | 100 |

According to GC analysis the used linoleic acid consisted of 67.96% linoleic acid (C18:2) and 25.92% oleic acid (C18:1).

The crème gel samples with and without 4-hydroxyacetophenone were coded A and B respectively. They were both divided into 2 parts. One part of each crème gel was kept at room temperature (RT) protected from light (Gel A1 and B1), the other part was exposed to 5 bar oxygen for 72 h at 60° C. using the Oxypress device from Mikrolab Aarhus (Gel A2 and B2). After the oxygen treatment, the crème gels A2, B2 and B1 were evaluated in direct comparison by 20 panellists. For olfactory evaluation, panellists were asked to rank the 3 samples according to their rancid smell with 1=the most rancid and 3=the least rancid off-odour. Results of the evaluation are given in the following Table 9:

TABLE 9

Results from olfactory evaluation

| | Number (percentage) of volunteers giving the score for the sample | | |
|---|---|---|---|
| Score | A2 (0.5% 4-hydroxy-acetophenone) Oxypress | B2 (Placebo) Oxypress | B1 (Placebo) RT protected from light |
| 1 (most rancid) | 6 (30%) | 14 (70%) | 0 (0%) |
| 2 | 9 (45%) | 6 (30%) | 5 (25%) |
| 3 (least rancid) | 5 (25%) | 0 (0%) | 15 (75%) |

The results clearly prove the odour stabilizing efficacy of 4-hydroxyacetophenone: In comparison with placebo B1, which was stored at RT protected from light, 70% of the volunteers ranked the Oxypress treated placebo B2 as the most rancid. Through the utilization of 4-hydroxyacetophenone in the crème gel the obtained Gel A2 shows an obviously improved odour stability under the same Oxypress condition as placebo B2, and 45% of the volunteers scored sample A2 with score 2 and 25% with 3 (least rancid).

It can be undoubtedly concluded that the odour stability of the crème gel rich in linoleic acid can be significantly improved by the application of 4-hydroxyacetophenone according to the present invention.

Example 5

Cosmetic Formulation Examples

Table 10a and 10b present a number of formulations according to the invention
1=Anti-Aging Face Oil
2=Glittering Dry Oil for Body & Hair
3=Sublimating Hair Oil
4=BB Cream SPF 15
5=Baby Nappy Rash Cream—W/O
6=Soft renewal body wash scrub
7=Hair Butter
8=Lipstick
9=Lip Cream
10=Concealer Stick
11=Daily face cream SPF 20
12=Cream Shower Oil
13=Facial Cleansing gel
14=Mascara
15=Shampoo
16=Massage Cream
17=Bath oil
18=Skin lightening cream
19=Face gel
20=O/W Soaking lotion for baby care wet wipes
21=Anti-aging crème
22=APD Roll-on Emulsion TABLE 10a Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| 4-Hydroxyacetophenone (SymSave H) Hydroxyacetophenone | 0.3 | 0.5 | 0.5 |  |  |  | 1 |  |  | 0.5 |  |

TABLE 10a-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| SymSave DH<br>Pentylene Glycol, Hydroxyacetophenone, 1,2-Hexanediol, Caprylyl Glycol | | | | 1 | | 1 | | 0.8 | | | |
| SymOcide PH<br>Phenoxyethanol, Hydroxyacetophenone, Caprylyl Glycol, Water (Aqua) | | | | | 1 | | | | 1 | | 1 |
| Actipone *Laminaria Saccharina*<br>Glycerin, Aqua, *Laminaria Saccharina* Extract | | | | 2 | | | | | | | |
| Actipone Hortensia Root GW<br>Aqua, Glycerin, *Hydrangea Arborescens* Root Extract | | | | 1 | | | | | | | |
| Andiroba oil<br>*Carapa Guaianensis* Seed Oil | | | | | | 1 | | | | 2 | |
| Apricot seed oil<br>*Prunus Armeniaca* (Apricot) Kernel Oil | 3.5 | | | | | | | 3 | | | |
| Argan oil<br>*Argania Spinosa* Kernel Oil | | 4 | 9 | | | | | | 0.5 | | |
| Ascorbyl Palmitate<br>Ascorbyl Palmitate | | | | | | | | | | | 0.1 |
| Avocado oil<br>*Persea Gratissima* (Avocado) Oil | | | 8 | 2 | | | | | 2 | | |
| Beeswax<br>Cera Alba | | | | | | | 10 | | | 5 | |
| Bentone Gel GTCC V<br>Caprylic/Capric Triglyceride, Stearalkonium Hectorite, Propylene Carbonate | | 2 | | | | | | | | | |
| Biotive L-Arginine<br>Arginine | | | | | | | | | | | 0.2 |
| Black currant oil<br>*Ribes Nigrum* (Black Currant) Seed Oil | | | 2 | | | | | | | | |
| Borage oil<br>*Borago Officinalis* Seed Oil | 3 | | | | | | | | | | |
| Brazilian nut oil<br>*Bertholletia Excelsa* Seed Oil | | | | | | 3 | | | | | |
| Buriti oil<br>*Mauritia Flexuosa* Fruit Oil | | | | | | 1 | | | | | 1 |
| Calendula oil<br>*Glycine Soja* (Soybean) Oil, *Calendula Officinalis* Flower Extract | 2 | | | | | | | | | | |
| Candelilla Wax<br>*Euphorbia Cera* (Candelilla) Wax | | | | | | | | 6 | 3 | 15 | |
| Carbopol Ultrez 21<br>Acrylates/C10-30 Alkyl Acrylate Crosspolymer | | | | 0.2 | | 1.1 | | | | | |
| Carnauba Wax<br>*Cera Carnaubae depurata* | | | | | | | | 2 | | 5 | |
| Cera Bellina<br>Polyglyceryl-3 Beeswax | | | | | | | | 3 | | | |
| CeramideBio<br>Cetylhydroxyproline Palmitamide | | | 0.5 | | | | | | | | |
| Ceteareth-20<br>Ceteareth-20 | | | | | | | | 1.5 | | | |
| Cetiol CC<br>Dicaprylyl Carbonate | 10 | 8 | | | | | | | | | |
| Cetiol OE<br>Dicaprylyl Ether | 12 | 10 | | | | | | | | | |
| Citric acid (sol. 20%)<br>Citric Acid | | | | | | | 7.1 | | 0.2 | | |
| Cocoa butter<br>*Theobroma Cacao* (Cocoa) Seed Butter | | | | | | | | | 0.5 | | 2 |
| Coconut oil<br>*Cocos Nucifera* (Coconut) Oil | | 12 | Ad 100 | | | | | | | 3 | |
| Colorona Bordeaux<br>Mica, CI 77491 (1:1) | | | | | | | | 7.5 | | | |

TABLE 10a-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| Controx Ks Tocopherol, Hydrogenated Palm Glyceride Citrate | | | | | | | | 0.3 | | | |
| Corn oil Zea Mays (Corn) Oil | | 5 | | | | | | | | | |
| Cosmetic color Brown Powder CI 77891, CI 77492, CI 77491, CI 77499 | | | | 1 | | | | | | | |
| Covapate Uniblue LC 6721 Ricinus Communis (Castor) Seed Oil 53-65%, CI 42090 (Blue 1 Lake) 35-47% | | | | | | | | 0.1 | | | |
| Covapate Unired LC 3779 Ricinus Communis (Castor) Seed Oil 73-85%, CI 15850 15-27% (Red no. 7) | | | | | | | | 2 | | | |
| Covasilic 15 Silica Dimethyl Silylate | | | 3 | | | | | | | | |
| Crodasinic LS-30 Sodium Lauroyl Sarcosinate | | | | | | 3.5 | | | | | |
| Cupuaçu butter Theobroma Grandiflorum Seed Butter | | | | | 1 | | | 2 | | | |
| Cutina HR Powder Hydrogenated Castor Oil | | | | | 1.5 | | | | | | |
| CWD 8906 Wax Hydrogenated Vegetable Oil, CI 77891 (Titanium Dioxide) | | | | | | | | 4 | | | |
| DC 2-8566 Amino Fluid Amodimethicone | | | | | | | 1.5 | | | | |
| DC 2502 Fluid Cetyl Dimethicone | | | | | | | | | | 5 | |
| DC 345 Fluid Cyclomethicone | | | | | | | | | | 5 | |
| DC 556 Fluid Phenyl Trimethicone | | | | | | | 1.5 | | | 4 | |
| DC 593 Dimethicone, Trimethylsiloxysilicate | | | | | | | 4 | | | | |
| Dehymuls PGPH Polyglyceryl-2 Dipolyhydroxystearate | | | | | 5 | | | | | | |
| Dimethicone | | | | | | | | | | | 0.5 |
| Dimethicone | | | | | | | | | | | |
| Disodium EDTA | | | | 0.1 | | | 0.1 | | | | 0.1 |
| Disodium EDTA | | | | | | | | | | | |
| Dracorin CE Glyceryl Stearate Citrate | | | | | | | | | 3 | | |
| Dracorin GOC Glyceryl Oleate Citrate, Caprylic/Capric Triglyceride | | | | | | | 2 | | | | |
| Dragosantol 100 Bisabolol | | | | | | | | | | | 0.1 |
| Dragosine Carnosine | | | | 0.1 | | | | | | | |
| Dragoxat 89 Ethylhexyl Isononanoate | 10 | | | | | | 3 | | | 10 | 5 |
| Emulsiphos Potassium Cetyl Phosphate, Hydrogenated Palm Glycerides | | | | 2 | | | | | | | 2 |
| Eutanol G Octyldodecanol | | | | | | | | | 5 | | |
| Evening primrose oil Oenothera Biennis (Evening Primrose) Oil | | 2 | | | | | | | | | |
| Extrapone Corail Glycerin, Aqua, Hydrolyzed Corallina Officinalis | | | | | | | | | | | 1 |
| Extrapone Lotus Flower Aqua, Butylene Glycol, Nelumbo Nucifera Flower Extract | | | | | | 1 | | | | | |

TABLE 10a-continued

| Ingredients | 1 | 2 | 3 | 4 | 5 | 6 | 7 | 8 | 9 | 10 | 11 |
|---|---|---|---|---|---|---|---|---|---|---|---|
| Extrapone Seaweed Aqua, Butylene Glycol, *Fucus Vesiculosus* Extract | | | | 1 | | | | | | | |
| Food color Iron oxide Yellow E172 CI 77492 | | | | 0.1 | | | | | | | |
| Food color Titanium Dioxide Powder E171 CI 77891 | | | | 0.2 | | | | | | | |
| Fragrance Parfum | 1 | | 1.1 | 0.7 | | 1.5 | | 0.3 | | 0.5 | |
| Frescolat Plus Menthol, Menthyl Lactate | | | | | | 0.5 | | | | | |
| Frescolat X-Cool Menthyl Ethylamido Oxalate Glycerin | | | | | | 0.3 | | | | | |
| Glycerin | | | | 3 | 5 | | | | | | 3 |
| Grape seed oil *Vitis Vinifera* (Grape) Seed Oil | Ad 100 | 16 | | | | | 2 | | | | |
| Green Pigment CI 77288, Triethoxycaprylylsilane | | | | | | | | | | 0.85 | |
| Hemp oil *Cannabis Sativa* Seed Oil | | 2 | | | | | | | | | |
| Hydrolite-5 Pentylene Glycol | | | | | | | | 2 | 3 | | |
| Hydromoist O Water (Aqua), *Avena Sativa* (Oat) Peptide | | | | | | | | 2 | | | |
| Hydroviton Plus Water (aqua), Pentylene Glycol, Glycerin, Fructose, Urea, Citric acid, Sodium Hydroxide, Maltose, Sodium PCA, Sodium Chloride, Sodium Lactate, Trehalose, Allantoin, Sodium Hyaluronate, Glucose | | | | | | 3.0 | | | | | |
| Isoadipate Diisopropyl Adipate | | | | | | | | | | 12.7 | 5 |
| Isodragol Triisononanoin | | 3 | | | | | | 5 | 5 | 8 | |
| Jojoba oil *Simmondsia Chinensis* (Jojoba) Seed Oil | 10 | 17 | | 2.5 | 5 | | | 5 | | | |
| Jojoba Wax Flakes Hydrogenated Jojoba Oil | | | | | | | | | | | 1 |
| Keltrol CG-T Xanthan Gum | | | | 0.3 | | | | | 0.2 | | 0.1 |
| Lanette O Cetearyl Alcohol | | | | 1 | | | | | 3 | | 5 |
| Lanette 16 Cetyl Alcohol | | | | 1 | | | | | | | 1 |
| Lanette 22 Behenyl Alcohol | | | | | | | | | | | 1 |
| Linseed oil *Linum Usitatissimum* (Linseed) Seed Oil | | | | 2 | | | | | | | |
| Lipo *Luffa* 30/100 *Luffa Cylindrica* Fruit | | | | | | 1 | | | | | |
| *Lotus* Exfoliator 500 *Nelumbo Nucifera* Seed Powder | | | | | | 0.3 | | | | | |
| *Macadamia* oil *Macadamia Ternifolia* Seed Oil | | 2 | | | | 3 | | 4 | | | |
| Magnesium Sulfate Hepta Hydrate Magnesium Sulfate | | | | | 0.5 | | | | | | |
| Micropoly 250S Polyethylene | | | | 0.7 | | | | | | | |
| Monomuls 90-O18 Glyceryl Oleate | | | | | 1 | | | | | | |

TABLE 10a-continued

| Cosmetic formulations (amounts in % b.w.) | | | | | | | | | | | |
|---|---|---|---|---|---|---|---|---|---|---|---|
| Ingredients | 1 | 2 | 3 | 4 | 5 | 6 | 7 | 8 | 9 | 10 | 11 |
| *Murumuru* butter *Astrocaryum Murumuru* Seed Butter | | 2 | | | | | 4.5 | | | | |
| Neo Heliopan 357 Butyl Methoxydibenzoylmethane | | | | 3.3 | | | | | | | 3 |
| Neo Heliopan 303 Octocrylene | | | | 8 | | | | | | | |
| Neo Heliopan HMS Homosalate | | | | | 5 | | | | | | 10 |
| Neo Heliopan Hydro used as a 25% aq. Solution neutralized by arginine Phenylbenzimidazole Sulfonic Acid | | | | | | | | | | | 8 |
| Neo Heliopan OS Ethylhexyl Salicylate | | | | | | | | | | | 5 |
| Neutral oil Caprylic/capric triglyceride | Ad 100 | | | 3 | 8 | 8 | | | | | |
| Olive oil *Olea Europaea* (Olive) Fruit Oil | | | 9 | | | | | | | | |
| Orgasol Caresse Polyamide-5 | | | | | | | | | | | 1 |
| Ozokerite Wax 1899 Ozokerite | | | | | | | | | 2 | | |
| Panthenol Panthenol | | | | | | 0.5 | | | | | |
| Passion fruit oil *Passiflora Edulis* Seed Oil | | | | | | 3 | | 1 | | 2 | |
| PCL Liquid Cetearyl Ethylhexanoate, Isopropyl Myristate | 5 | | | | | | | | | | |
| PCL Liquid 100 Cetearyl Ethylhexanoate | | | | | 5 | | | | | | |
| PCL Solid Stearyl Heptanoate, Stearyl Caprylate | | | | | | | | | | 3 | |
| Peanut oil *Arachis Hypogaea* (Peanut) Oil | | | | | | 2 | | | | | |
| Perfume oil PFO1 | | 1.2 | | | | | | | | | 0.1 |
| Perfume oil PFO2 | | | | | | | 0.6 | | | | |
| Phytoconcentrole Camomile Bisabolol, Caprylic/Capric Triglyceride, *Chamomilla Recutita* Flower Extract | | 1 | | | | | | | | | |
| Phytoconcentrole Cotton *Glycine Soja* (Soybean) Oil, *Gossypium Herbaceum* (Cotton) Seed Oil | | | | 2 | | | | | | | |
| Pomgranate seed oil *Punica Granatum* (Pomegranate) Seed Oil | | 2 | | | | | | 2 | | | |
| Poppy oil *Papaver Orientale* (Poppy) Seed Oil | | | | | 1 | | | | | | |
| Potassium Sorbate Potassium Sorbate | | | | | | | | | | 0.3 | |
| Protelan AGL Sodium Lauroyl Glutamate | | | | | | 8 | | | | | |
| Proteol APL Sodium Cocoyl Apple Amino Acids | | | | | | 2 | | | | | |
| Pumpkin seed oil *Cucurbita Pepo* (Pumpkin) Seed Oil | | | | 5 | | | | | | | |
| PVP K-90 PVP | | | | | | | | | 2 | | |
| Ronaflair M-Sphere Mica (CI 77019) 99%, Silica 1% | | | | | | | | | 7.5 | | |
| *Ricinus* Oil, pharm. raff *Ricinus Communis* (Castor) Seed Oil | | | | | | | | | Ad 100 | | |

TABLE 10a-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| Safflower oil *Carthamus Tinctorius* (Safflower) Seed Oil | 5 | | | | | | | 3 | | | |
| Sesame oil *Sesamum Indicum* (Sesame) Seed Oil | | | | 1 | | | | | | 3 | |
| Shea butter *Butyrospermum Parkii* (Shea) Butter | | | | 2.5 | | | | | | Ad 100 | 3 |
| Simugel EG Sodium Acrylate/Sodium Acryloyldimethyl Taurate Copolymer, Isohexadecane, Polysorbate 80 | | | | | | | | | | | 1 |
| Sodium Hydroxide, 10% solution Aqua, Sodium Hydroxide | | | | 0.3 | | 2.1 | | | | | |
| Soybean oil *Glycine Soja* (Soybean) Oil | | 7 | | | | | | | | | |
| Stearic acid Stearic Acid | | | | | | | | 5 | | | |
| Sunflower oil *Helianthus Annuus* (Sunflower) Seed Oil | | 12 | | | | | | | | | |
| Sunshine Crystal Bronze Synthetic Fluorphlogopite CI 77491 | | 0.2 | | | | | | | | | |
| Sunshine Crystal Golden Synthetic Fluorphlogopite CI 77891 CI 77491 | | 0.4 | | | | | | | | | |
| Sweet almond oil *Prunus Amygdalus Dulcis* (Sweet Almond) Oil | 5 | 14 | | | | 7 | 3 | | | | |
| Sym3D Hydroxymethoxyphenyl Propylmethylmethoxybenzofuran | | | | | | | | | 0.25 | | |
| SymBronze Caprylic/Capric Triglyceride, *Isochrysis Galbana* Extract | | | 2 | | | | | | | | |
| SymCalmin Butylene Glycol, Pentylene Glycol, Hydroxyphenyl Propamidobenzoic Acid | | | | | 1 | | | | | | |
| SymCare O Hexyldecanol, Pentylene Glycol, 4-t-Butylcyclohexanol, Bisabolol, Cetylhydroxyproline Palmitamide, Hydroxyphenyl Propamidobenzoic Acid, Stearic Acid, *Brassica Campestris* (Rapeseed) Sterols, *Zingiber Officinale* (Ginger) Root Extract | | | | | | | | | | 2 | |
| SymClariol Decylene Glycol | | | | | | | | | | 0.3 | |
| SymFinity 1298 *Echinacea Purpurea* Extract | | | | | | | | | | | 0.1 |
| SymGlucan Aqua, Glycerin, Beta-Glucan | | | | | | 1 | | | | | |
| SymMatrix Maltodextrin, *Rubus Fructicosus* (Blackberry) Leaf Extract | | | | | | | | | | | 0.1 |
| SymMollient S Cetearyl Nonanoate | 5 | | | | | | | 5 | | | |
| SymRelief 100 Bisabolol, *Zingiber Officinale* (Ginger) Root Extract | | | | | | | | | 0.2 | | |
| SymRepair 100 Hexyldecanol, Bisabolol, Cetylhydroxyproline Palmitamide, Stearic Acid, *Brassica Campestris* (Rapeseed) Sterols | 2 | | | | | | | | | | |

TABLE 10a-continued

Cosmetic formulations (amounts in % b.w.)

| Ingredients | 1 | 2 | 3 | 4 | 5 | 6 | 7 | 8 | 9 | 10 | 11 |
|---|---|---|---|---|---|---|---|---|---|---|---|
| SymSitive 1609 Pentylene Glycol, 4-t-Butylcyclohexanol |  |  |  |  |  |  |  |  |  |  | 1 |
| Tamanu oil Calophyllum Inophyllum Seed Oil |  |  |  |  | 0.2 |  |  |  |  |  |  |
| Tegosoft TN C12-15 Alkyl Benzoate |  |  |  |  |  |  |  |  |  |  | 4 |
| Tetrasodium EDTA Tetrasodium EDTA |  |  |  |  | 0.1 |  |  |  |  |  |  |
| Titan dioxide Titan dioxide |  |  |  |  | 4 |  |  |  |  |  |  |
| Tocopherol Tocopherol |  |  |  |  |  |  |  |  | 0.1 |  |  |
| Tocopheryl acetate Tocopheryl acetate |  |  |  |  |  | 0.5 |  |  |  |  |  |
| Triethanolamine 99% Triethanolamine |  |  |  |  |  |  |  | 2.5 |  |  |  |
| Viamerine WH 60 Hydroxystearic/Linolenic/Oleic Polyglycerides |  |  |  |  |  |  |  |  | 1 |  |  |
| Vitamin F Ethyl Ester Ethyl Linoleate, Ethyl Linolenate, Ethyl Oleate |  | 1 |  |  |  |  |  |  |  |  |  |
| Water Aqua |  |  |  | Ad 100 | Ad 100 | Ad 100 | Ad 100 |  | Ad 100 |  | Ad 100 |
| Wheat germ oil Triticum Vulgare (Wheat) Germ Oil |  |  |  |  | 2 |  |  |  |  |  |  |
| White pigment CI 77891, Ricinus (Castor) seed oil |  |  |  |  |  |  |  |  |  | 7 |  |
| Yellow pigment CI 77492, Triethoxycaprylylsilane |  |  |  |  |  |  |  |  |  | 0.15 |  |
| Zinc oxide Zinc oxide |  |  |  |  | 10 |  |  |  |  |  |  |

TABLE 10b

Cosmetic formulations (amounts in % b.w.)

| Ingredients | 12 | 13 | 14 | 15 | 16 | 17 | 18 | 19 | 20 | 21 | 22 |
|---|---|---|---|---|---|---|---|---|---|---|---|
| 4-Hydroxyacetophenone (SymSave H) Hydroxyacetophenone | 0.5 | 0.5 | 0.2 | 0.3 |  | 0.5 |  |  |  | 0.5 | 0.2 |
| SymSave DH Pentylene Glycol, Hydroxyacetophenone, 1,2-Hexanediol, Caprylyl Glycol |  |  |  |  | 1 |  |  | 1 |  |  |  |
| SymOcide PH Phenoxyethanol, Hydroxyacetophenone, Caprylyl Glycol, Water (Aqua) |  |  |  |  |  |  | 1 |  | 1 |  |  |
| Actipone Ginger Juice (Organic) GW Glycerin, Zingiber Officinale (Ginger) Root Juice, Water (Aqua) |  |  |  |  |  |  |  | 1 |  |  |  |
| Andiroba oil Carapa Guaianensis Seed Oil |  |  |  |  | 1 |  |  |  |  |  |  |
| Antil 127 PEG-120 Methyl Glucose Dioleate |  |  |  | q.s. |  |  |  |  |  |  |  |
| Apricot seed oil Prunus Armeniaca (Apricot) Kernel Oil | 0.5 |  |  |  |  |  |  |  |  |  |  |
| Argan oil Argania Spinosa Kernel Oil |  |  | 5 |  |  |  |  |  |  |  |  |
| Aristoflex Velvet Polyacrylate Crosspolmer-11 |  |  |  |  |  |  |  |  | 0.8 |  |  |

TABLE 10b-continued

| Cosmetic formulations (amounts in % b.w.) | | | | | | | | | | | |
|---|---|---|---|---|---|---|---|---|---|---|---|
| Ingredients | 12 | 13 | 14 | 15 | 16 | 17 | 18 | 19 | 20 | 21 | 22 |
| Avocado oil<br>*Persea Gratissima* (Avocado) Oil | 5 | | | | | | | | | 3 | |
| Beeswax<br>Cera Alba | | | 3 | | | | | | | | |
| Belsil DMC 6038<br>PEG 15-Methyl Ether Dimethicone | | | | | | | | | 2 | | |
| Black currant oil<br>*Ribes Nigrum* (Black Currant) Seed Oil | | | | | 3 | | | | | | |
| Borage oil<br>*Borago Officinalis* Seed Oil | | | | | 5 | | | | | | |
| Brazilian nut oil<br>*Bertholletia Excelsa* Seed Oil | | | | 0.5 | | | | | | | |
| Buriti oil<br>*Mauritia Flexuosa* Fruit Oil | | | | | | | | 0.2 | | | 0.1 |
| Carbopol Ultrez 10<br>Carbomer | | | | | 0.25 | | | | | | 0.6 |
| Castor Oil<br>*Ricinus Communis* (Castor) Seed Oil | 8 | | | | | | | | | | |
| Citric acid 10% solution<br>Citric acid | 0.25 | | | | | | 0.15 | | 0.1 | | |
| Cocamidopropyl Betaine 38%<br>Cocamidopropyl Betaine | | | | 5 | | | | | | | |
| Cocoa butter<br>*Theobroma Cacao* (Cocoa) Seed Butter | | | | | | 1 | | | | | |
| CI 12.490 (sol. 0.5%)<br>CI 12490 | | | | | 0.27 | | | | | | |
| CI 14.720 (sol. 0.5%)<br>CI 14720 | | | | | | | | 0.07 | | | |
| CI 19.140 (sol. 0.5%)<br>CI 19140 | | | | | 0.3 | | | 0.03 | | | |
| CI 42.090 (sol. 0.5%)<br>CI 42090 | | | | | 0.02 | | | | | | |
| COSMETIC COLOUR BLACK<br>C.I. 77492, 77499 | | | 14 | | | | | | | | |
| Crinipan AD<br>Climbazole | | | | 0.3 | | | | | | | |
| Cupuaçu butter<br>*Theobroma Grandiflorum* Seed Butter | | | | | 2 | | | | | | |
| Cutina FS 45<br>Stearic Acid, Palmitic Acid | | | 1 | | | | | | | | |
| DC 245 Fluid<br>Cyclopentasiloxane | | | | | 10 | | | 4 | | | |
| DC 345 Fluid<br>Cyclomethicone | | | | | | | | | 0.2 | | |
| Diammonium Citrate<br>Diammonium Citrate | 0.1 | | | | | | | | | | |
| Dimethicone<br>Dimethicone | | | | | | | | | | 0.5 | |
| Dissodium EDTA<br>Dissodium EDTA | | | | | 0.1 | | 0.1 | 0.1 | | | |
| Dracorin 100 SEP<br>Glyceryl Stearate, PEG-100 Stearate | | | | | | | | | | 7 | |
| Dracorin GMS<br>Glyceryl stearate | | | 2 | | | | 4 | | | 2.5 | 6 |
| Dragoderm<br>Glycerin, *Triticum Vulgare* Gluten, Aqua | | | | 0.5 | | | | | | | |
| Dragosantol<br>Bisabolol, Farnesol | 0.2 | | | | | | | | 0.1 | | 0.05 |
| Dragoxat 89<br>Ethylhexyl Isononanoate | | | 3 | | 6 | | 4 | | | 5 | |
| Dry Flo Pure<br>Aluminum Starch Octenylsuccinate | | | | | 3 | | | | | | |
| Emulsiphos<br>Potassium Cetyl Phosphate, Hydrogenated Palm Glycerides | | | 2 | | 3 | | 1.3 | | | | |

TABLE 10b-continued

| Cosmetic formulations (amounts in % b.w.) | | | | | | | | | | | |
|---|---|---|---|---|---|---|---|---|---|---|---|
| Ingredients | 12 | 13 | 14 | 15 | 16 | 17 | 18 | 19 | 20 | 21 | 22 |
| Eumulgin B2 Ceteareth-20 | | | | | | | | | 2.5 | | 6 |
| Eutanol G Octyldodecanol | | | | | | | | | | | 8 |
| Evening primrose oil *Oenothera Biennis* (Evening Primrose) Oil | 5 | | | | | | | | | | |
| Extrapone Nutgrass (Motha) Root GW Water (Aqua), Glycerin, *Cyperus Rotundus* Root extr. | | | | | | | | 0.5 | | | |
| Fragrance Perfum | | 0.2 | | 0.5 | | 8 | | 0.3 | 0.1 | | 1 |
| Frescolat X-Cool Menthyl Ethylamido Oxalate | | | | | | | | 0.1 | | | |
| Glycerin Glycerin | | 15 | | 0.5 | | | 3 | | 3 | 2 | 5 |
| Grape seed oil *Vitis Vinifera* (Grape) Seed Oil | | | | | | 10 | 1.5 | | | | |
| Hydrolite 5 Pentylene Glycol | | | | | | | 3 | 2 | | 5 | |
| Isodragol Triisononanoin | | | | | | | 3 | | | | |
| Isopropyl Myristate Isopropyl Myristate | | | | | | | | | 0.5 | | |
| Isopropyl Palmitate Isopropyl Palmitate | | | | | | | | | 3 | | |
| Jojoba oil *Simmondsia Chinensis* (Jojoba) Seed Oil | | | | 0.5 | | | 1.5 | | | | |
| Lanette 16 Cetyl Alcohol | | | 1 | | 4 | | | | | 2 | 1 |
| Lanette O Cetearyl Alcohol | | | | | 3.6 | | 3.5 | | 2.5 | | |
| Marlinat 242/90 M MIPA Laureth Sulfate, Propylene Glycol | | | | 15 | | | | | | | |
| Marlowet CG PEG-18 Castor Oil Dioleate | | | | 2 | | | | | | | |
| Medium Mineral Oil Paraffinum Liquidum | | | | | | Ad 100 | | | | | |
| Mineral oil Paraffinum Liquidum | | | | | | | | | 2 | | |
| Mulsifan CPA Laureth-4 | | | | | | | 10 | | | | |
| *Murumuru* butter *Astrocaryum Murumuru* Seed Butter | | | | | 2 | | | | | | |
| Neo Heliopan BB Benzophenone-3 | | | | | | | | 0.5 | | | |
| Neutral oil Caprylic/capric triglyceride | | 25 | | | | | | | | | |
| Olive oil *Olea Europaea* (Olive) Fruit Oil | | Ad 100 | | | | | | | 0.5 | | |
| Oxynex ® ST Liquid Diethylhexyl Syringylidene Malonate, Caprylic/Capric Triglyceride | | | | | | 0.3 | | | | | |
| Panthenol Panthenol | 0.5 | | | | | | | | | | |
| Paracera M Cera Microcrystalina | | | | 2 | | | | | | | |
| PCL Liquid 100 Cetearyl Ethylhexanoate | | | | 1 | | | | | | | |
| PCL Solid Stearyl Heptanoate, Stearyl Caprylate | | | | | | | 1 | | | | |
| Perfume oil PFO1 | 2 | | | | | | | | | 0.3 | |
| Perfume oil PFO2 | | | | | | 0.6 | | | | | |
| Phytoconcentrole Arnica *Glycine Soja* (Soybean) Oil, *Arnica Montana* Flower Extract | | | 1 | | | | | | | | |

TABLE 10b-continued

| | Cosmetic formulations (amounts in % b.w.) | | | | | | | | | | |
|---|---|---|---|---|---|---|---|---|---|---|---|
| Ingredients | 12 | 13 | 14 | 15 | 16 | 17 | 18 | 19 | 20 | 21 | 22 |
| Phytoconcentrole Camomile *Glycine Soja* (Soybean) Oil, Bisabolol, *Chamomilla Recutita* (Matricaria) Flower Extract | 3 | | | | | | | | | | |
| Plantacare 1200 UP Lauryl Glucoside | | | | 0.5 | | | | | | | |
| Pluronic L-31 Poloxamer 101 | 3 | | | | | | | | | | |
| Polyglyceryl-5 Oleate Polyglyceryl-5 Oleate | | 6 | | | | | | | | | |
| Polyquaternium-10 Polyquaternium-10 | | | | 0.3 | | | | | | | |
| Propylene Glycol Propylene Glycol | | | 12 | | | | | | | | |
| PVP-K 30 Powder PVP | | | 3 | | | | | | | | |
| Reach 501 Aluminium Chlorhydrate | | | | | | | | | | | 15 |
| Retinol SU 10 *Glycine Soja* (Soybean) Oil, Retinol | | | | | | | | | 0.2 | | |
| Shea butter *Butyrospermum Parkii* (Shea) Butter | 1 | | 2 | | | | | | | | 0.1 |
| Sodium Chloride Sodium Chloride | | | | 1.5 | | | | | | | |
| Sodium Hydroxide (sol. 30%) Sodium Hydroxide | | | | | | q.s. | | q.s. | | 0.05 | |
| Solubilizer PEG-40 Hydrogenated Castor Oil, Trideceth-9, Propylene Glycol, Water (Aqua) | | | | | | | | 0.5 | | | |
| Soybean oil *Glycine Soja* (Soybean) Oil | Ad 100 | | | | | | | | | | |
| Super Hartolan Lanolin Alcohol | | | | | | | | | 0.2 | | |
| Sweet almond oil *Prunus Amygdalus Dulcis* (Sweet Almond) Oil | | | | | | | | | 2 | | |
| SymCalmin Butylene Glycol, Pentylene Glycol, Hydroxyphenyl Propamidobenzoic Acid | | | | 1 | | | | | | | |
| SymDiol 68 Caprylyl Glycol, 1,2-Hexanediol | | | | | | | | | | | 0.8 |
| SymHair Force 1631 Pentylene Glycol, *Isochrysis Galbana* Extract | | | 0.5 | | | | | | | | |
| SymMollient S Cetearyl Nonanoate | | | 1 | | | | | | | | |
| SymOcide PS Phenoxyethanol, Decylene Glycol, 1,2-Hexanediol | | | | 0.8 | | | | | | 0.5 | |
| SymPeptide 226EL Water (Aqua), Glycerin, Myristoyl Pentapeptide-17 | | | 2 | | | | | | | | |
| SymRelief 100 Bisabolol, *Zingiber Officinalis* (Ginger) Root Extract | | | | | | | | | 0.2 | | |
| SymTriol Caprylyl Glycol, 1,2-Hexanediol, Methylbenzyl Alcohol | | | 0.8 | | | | | | | | |
| SymWhite 377 Phenylethyl Resorcinol | | | | | | | | | 0.5 | | |
| Tagat L2 PEG-20 Glyceryl Laurate | | | | | | | | | | 2.5 | |
| Tocopheryl acetate Tocopheryl acetate | | | | | | | | | 0.3 | | |
| Triethanolamine 99% Triethanolamine | | | 0.7 | | | | | | | | |
| Tween 20 Polysorbate 20 | | | | | | | | | | | 0.5 |

TABLE 10b-continued

| Ingredients | 12 | 13 | 14 | 15 | 16 | 17 | 18 | 19 | 20 | 21 | 22 |
|---|---|---|---|---|---|---|---|---|---|---|---|
| Vaseline | | | 3 | | | | | | | | |
| Petrolatum | | | | | | | | | | | |
| Water | | App. 1.43 | Add 100 | Ad 100 | Ad 100 | | Ad 100 | Ad 100 | Ad 100 | Ad 100 | Ad 100 |
| Aqua | | | | | | | | | | | |
| Xanthan gum | | | 0.5 | | 0.25 | | 0.2 | | | | |
| Xanthan gum | | | | | | | | | | | |
| Zetesol 100 | 43 | | | | | | | | | | |
| MIPA-Laureth Sulfate, Laureth-4, Cocamide DEA | | | | | | | | | | | |

Composition of perfume oils PFO1 and PFO2 (DPG=dipropylene glycol) are given in Tables 11 and 12.

TABLE 11

Perfume oil PFO1

| Component/Name | Parts b.w. |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE 12

Perfume oil PFO2

| Component/Name | Parts b.w. |
|---|---|
| Benzyl acetate | 60.00 |
| Citronellyl acetate | 60.00 |
| Cyclamenaldehyde (2-methyl-3-(4-isopropylphenyl)propanal) | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |

TABLE 12-continued

Perfume oil PFO2

| Component/Name | Parts b.w. |
|---|---|
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

Example 6

Gelatine Capsules for Direct Consumption

TABLE 13

Gelatine capsule for direct consumption

| RAW MATERIAL NAME | WEIGHT % | | | |
|---|---|---|---|---|
| | I | II | III | IV |
| Gelatine shell: | | | | |
| Glycerin | 2.014 | 2.014 | 2.014 | 2.014 |
| Gelatine 240 Bloom | 7.91 | 7.91 | 7.91 | 7.91 |
| Sucralose | 0.065 | 0.065 | 0.065 | 0.065 |
| Allura Red | 0.001 | 0.006 | \ | \ |
| Brillant Blue | \ | 0.005 | \ | 0.005 |
| Core composition: | | | | |
| Borage oil | \ | \ | Ad 100 | \ |
| Evening primrose oil | Ad 100 | \ | \ | \ |
| Wheat germ oil | \ | Ad 100 | \ | \ |
| Salmon oil | \ | \ | \ | Ad 100 |
| Aroma | \ | 12.0 | 1.0 | \ |
| 4-Hydroxyacetophenone | 0.1 | 0.05 | 0.05 | 0.1 |

Aroma used in the gelatine capsule had the following composition (in wt. %): 0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule suitable for direct consumption (produced in an analogous way to WO 2004/050069) had a diameter of 5 mm and the weight ratio of core material to shell material was 90:10. The capsule opened in the mouth in less than 10 seconds and dissolved completely in less than 50 seconds.

Example 7

Flavoured Vegetable Oils for Culinary Use

TABLE 14

Flavoured vegetable oils for culinary use

| RAW MATERIAL NAME | WEIGHT % | | | |
|---|---|---|---|---|
| | I | II | III | IV |
| Basil extract | 0.3 | \ | 0.1 | \ |
| Corn oil | \ | \ | Ad 100 | \ |
| Chili extract | \ | 0.1 | \ | \ |
| Lemon flavor | \ | \ | \ | 1 |
| Olive oil | \ | \ | 30 | \ |
| 4-Hydroxyacetophenone | 0.05 | 0.2 | 0.1 | 0.1 |
| Pumpkin seed oil | \ | 5 | \ | \ |
| Rapeseed oil | \ | \ | \ | Ad 100 |
| Soybean oil | \ | Ad 100 | \ | \ |
| Sunflower oil | Ad 100 | 50 | \ | \ |
| Tomato flavor | \ | \ | 0.5 | \ |
| Walnut oil | 3 | \ | \ | \ |

These vegetable oils can be used to flavour various kinds of warm or cold dishes.

What is claimed is:

1. A method for stabilizing the taste and/or odor of mono- or polyunsaturated C8-C22 fatty acid or its monohydric or polyhydric $C_1$-$C_{18}$ aliphatic alcohol ester in a composition containing the same, comprising the steps of
    adding 4-hydroxyacetophenone to said mono- or polyunsaturated $C_8$-$C_{22}$ fatty acid or its monohydric or polyhydric $C_1$-$C_{18}$ aliphatic alcohol ester, in an amount effective to prevent oxidation and rancidity of said mono- or polyunsaturated $C_8$-$C_{22}$ fatty acid or its monohydric or polyhydric $C_1$-$C_{18}$ aliphatic alcohol ester,
    forming a composition containing both said 4-hydroxyacetophenone and said mono- or polyunsaturated $C_8$-$C_{22}$ fatty acid or its monohydric or polyhydric $C_1$-$C_{18}$ aliphatic alcohol ester, with said 4-hydroxyacetophenone present in an amount from 0.01 to 5 wt. %, based on the total weight of said composition,
    preventing oxidation and rancidity of said mono- or polyunsaturated $C_8$-$C_{22}$ fatty acid or its monohydric or polyhydric $C_1$-$C_{18}$ aliphatic alcohol ester for at least two months after forming said composition, and
    stabilizing said mono- or polyunsaturated $C_8$-$C_{22}$ fatty acid or its monohydric or polyhydric $C_1$-$C_{18}$ aliphatic alcohol ester for at least two months after forming said composition.

2. The method of claim 1, wherein the mono- or polyunsaturated $C_8$-$C_{22}$ fatty acid or its monohydric or polyhydric $C_1$-$C_{18}$ alkyl alcohol ester comprises
    (b-1) at least one acyl compound of formula (II)

wherein
    R stands for hydrogen atom or an $C_1$-$C_{18}$ alkyl group, and
    X represents a mono- or polyunsaturated $C_8$-$C_{22}$ acyl group, and/or
    (b-2) at least one acylglycerol compound of formula (III)

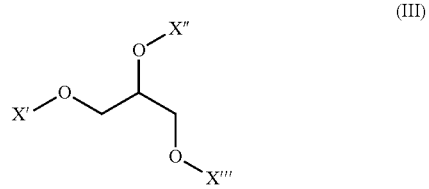

wherein
    X', X" and X'" independently of one another represents a hydrogen atom or a saturated or mono- or polyunsaturated $C_8$-$C_{22}$ acyl group, with the proviso that X', X" and X'" do not simultaneously represent a hydrogen atom and at least one of X', X" and X'" being an unsaturated acyl group.

3. The method of claim 1, where the added amount of 4-hydroxyacetophenone is from 0.05 to 2 wt. %, based on the total weight of the composition comprising both said 4-hydroxyacetophenone and said mono- or polyunsaturated $C_8$-$C_{22}$ fatty acid or its monohydric or polyhydric $C_1$-$C_{18}$ aliphatic alcohol ester.

4. The method of claim 3, where the added amount of 4-hydroxyacetophenone is from 0.1 to 1 wt. %, based on the total weight of the composition comprising both said 4-hydroxyacetophenone and said mono- or polyunsaturated $C_8$-$C_{22}$ fatty acid or its monohydric or polyhydric $C_1$-$C_{18}$ aliphatic alcohol ester.

5. The method of claim 1, wherein said fatty acid or ester is a blend of oleic, linoleic, palmitic and stearic acids.

6. The method of claim 1, wherein said fatty acid or ester is a blend of oleic, linoleic, palmitic and palmitoleic acids.

7. The method of claim 1, wherein said fatty acid or ester is a blend of oleic and linoleic acids.

8. The method of claim 1, wherein said fatty acid is linoleic acid.

* * * * *